US009682126B2

(12) United States Patent
Sakai et al.

(10) Patent No.: US 9,682,126 B2
(45) Date of Patent: Jun. 20, 2017

(54) POSTPRANDIAL GASTROKINETIC AGENT

(71) Applicants: ZERIA PHARMACEUTICAL CO., LTD., Chuo-ku (JP); SAITAMA UNIVERSITY, Saitama-shi (JP)

(72) Inventors: Takafumi Sakai, Saitama (JP); Ichiro Sakata, Saitama (JP); Kayuri Kuroda, Saitama (JP); Makoto Yoshimura, Chuo-ku (JP)

(73) Assignees: ZERIA PHARMACEUTICAL CO., LTD., Chuo-ku (JP); SAITAMA UNIVERSITY, Saitama-shi (JP)

( * ) Notice: Subject to any disclaimer, the term of this patent is extended or adjusted under 35 U.S.C. 154(b) by 0 days.

(21) Appl. No.: 14/779,730

(22) PCT Filed: Feb. 10, 2014

(86) PCT No.: PCT/JP2014/053060
§ 371 (c)(1),
(2) Date: Sep. 24, 2015

(87) PCT Pub. No.: WO2014/156339
PCT Pub. Date: Oct. 2, 2014

(65) Prior Publication Data
US 2016/0051630 A1    Feb. 25, 2016

(30) Foreign Application Priority Data

Mar. 25, 2013  (JP) ................. 2013-062726

(51) Int. Cl.
*A61K 38/22* (2006.01)
*A61K 38/25* (2006.01)
*A61K 45/00* (2006.01)
*A61K 45/06* (2006.01)

(52) U.S. Cl.
CPC .......... *A61K 38/2214* (2013.01); *A61K 38/22* (2013.01); *A61K 38/25* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,418,224 A * | 5/1995 | Hoeltje | ................. | C07H 17/08 514/28 |
| 5,470,830 A * | 11/1995 | Macielag | ............... | C07K 14/63 514/21.4 |
| 5,734,012 A * | 3/1998 | Dharanipragada | .... | C07K 14/63 530/317 |
| 5,912,235 A * | 6/1999 | Hoeltje | ................. | C07H 17/08 514/28 |
| 6,380,158 B1 * | 4/2002 | Sheppard | ............. | C07K 14/575 530/300 |
| 7,179,886 B1 * | 2/2007 | Feighner | .............. | C07K 14/705 435/320.1 |
| 7,385,026 B1 * | 6/2008 | Kangawa | .............. | A61K 9/0019 530/324 |
| RE42,013 E  * | 12/2010 | Hoveyda | .............. | C07K 5/0812 514/21.1 |
| 7,932,231 B2 * | 4/2011 | Datta | ..................... | C07K 14/60 424/551 |
| 9,371,369 B2 * | 6/2016 | Schellenberger | .... | C07K 14/001 |
| 2002/0192709 A1 * | 12/2002 | Carreras | ............... | C07H 21/04 435/7.1 |
| 2005/0065156 A1 * | 3/2005 | Li | ........................ | C07D 471/20 514/248 |
| 2005/0080116 A1 * | 4/2005 | Li | ........................ | A61K 31/495 514/364 |
| 2006/0293243 A1 * | 12/2006 | Puri | ..................... | A61K 9/0019 514/9.7 |
| 2007/0025991 A1 * | 2/2007 | Pothoulakis | .......... | A61K 38/25 424/145.1 |
| 2007/0232657 A1 * | 10/2007 | Ahmed | ................ | C07D 405/14 514/320 |
| 2008/0261873 A1 * | 10/2008 | Geesaman | ............. | A61K 38/25 514/6.9 |
| 2008/0306083 A1 * | 12/2008 | MacDonald | ......... | C07D 401/04 514/253.1 |
| 2009/0143310 A1 * | 6/2009 | Polvino | .................. | A61K 31/33 514/1.1 |
| 2009/0275511 A1 * | 11/2009 | Dong | ..................... | C07K 14/60 514/6.9 |
| 2010/0179168 A1 * | 7/2010 | Blaney | .................. | C07C 311/29 514/254.1 |

(Continued)

FOREIGN PATENT DOCUMENTS

WO    WO 2009/082426 A1    7/2009

OTHER PUBLICATIONS

Kamerling et al. Exogenous motilin affects postprandial proximal gastric motor function and visceral sensation, Digestive diseases and Sciences, 47, 1732-1736, 2002.*
Sako et al. EM574, an erythromycin derivative, improves delayed gastric emptying in semi-solid meals in conscious dogs. Eur. J. Phamacol. 395, 165-172, 2000.*
Shindo et al. Comparison of gastric emptying and plasma ghrelin levels in patients with functional dyspepsia and non-erosive reflux disease. Digestion, 79, 65-72, 2009.*
Sakahara et al. Physiological characteristics of gastric contractions and circadian gastric motility in the free-moving conscious house musk shrew (*Suncus murinus*). Am. J. Physiol. Integr. Comp. Physiol., 299, R1106-R1113, 2010.*

(Continued)

*Primary Examiner* — Elly-Gerald Stoica
(74) *Attorney, Agent, or Firm* — Oblon, McClelland, Maier & Neustadt, L.L.P.

(57) ABSTRACT

To provide a therapeutic agent for gastrointestinal disorder such as diabetic gastroparesis. A postprandial gastrokinetic agent containing (A) ghrelin or a ghrelin agonist and (B) motilin or a motilin agonist as active ingredients, in which both the ingredients (A) and (B) are administered so as to act on the stomach after food intake.

19 Claims, 18 Drawing Sheets

(56) References Cited

U.S. PATENT DOCUMENTS

| | | | | |
|---|---|---|---|---|
| 2010/0317693 | A1* | 12/2010 | Watanabe | C07D 401/04 514/312 |
| 2012/0010157 | A1* | 1/2012 | Polvino | A61K 31/33 514/21.8 |
| 2013/0085105 | A1* | 4/2013 | Deasy | A61K 9/0014 514/11.1 |
| 2015/0037359 | A1* | 2/2015 | Schellenberger | C07K 5/0205 424/178.1 |

OTHER PUBLICATIONS

International Search Report issued Apr. 28, 2014, in PCT/JP2014/053060 filed Feb. 10, 2014.

Written Opinion of the International Searching Authority issued Apr. 28, 2014, in PCT/JP2014/053060 filed Feb. 10, 2014.

I. Sakata et al, "Model animal for studies of food intake and gastrointestinal motility—a small mammal Suncus which produces motilin and ghrelin-", G. I. Research, (Feb. 2013), vol. 21, No. 1, pp. 25 to 30.

K. Koike et al., "Suncus as a model animal for studies of gastrointestinal motility—Identification of motilin and ghrelin and contractions of the intestinal tract-", Comparative Endocrinology, (2011), vol. 37, No. 142, 8 pages.

T. Sakai et al., "Analysis of a gastrointestinal contraction control mechanism using Suncus—Cooperative action of motilin and ghrelin-", Journal of Smooth Muscle Research, vol. 16, No. 1, (2012), 3 pages.

A. Mondal et al., "Motilin and ghrelin regulate gastric contractions via the myenteric plexus in Suncus murinus (house musk shrew)", Journal of Smooth Muscle Research, (2012), vol. 16, No. 1, 3 pages.

T. Ohno et al., Gastrointestinal motility function control and dysfunction, Basic gastrointestinal motility and its control mechanism, Journal of Clinical and Experimental Medicine, (2011), vol. 238, No. 10, 7 pages.

E. Mochiki et al., "Correlation between the brain and the nerve, Goal of studies on nerve-gastroenterology, Control mechanism and pathology of the gastrointestinal motility function, Motilin,—Fasting contractions mechanism by the intestinal tract nerve system, Motilin and fasting contractions", Journal of Clinical and Experimental Medicine, vol. 201, No. 1, (2002), 6 pages.

Y. Falken et al., "Actions of prolonged ghrelin infusion on gastrointestinal transit and glucose homeostasis in humans", Neurogastroenterology Motility, vol. 22, (2010), pp. e-192 to e-200.

M. Binn et al., "Ghrelin gastrokinetic action in patients with neurogenic gastroparesis", Peptides, vol. 27, (2006), pp. 1603-1606.

N. Ejskjaer et al., "A phase 2a, randomized, double-blind 28-day study of TZP-102 a ghrelin receptor agonist for diabetic gastroparesis", Neurogastroenterology & Motility, vol. 25, (2013), pp. e140-e150.

T.L. Peeters et al., "Effect of Motilin on Gastric Emptying in Patients with Diabetic Gastroparesis", gastroenterology, vol. 102, No. 1, (Jan. 1992), pp. 97-101.

R.W. McCallum et al., "Clinical trial: effect of mitemcinal (a motilin agonist) on gastric emptying in patients with gastroparesis—a randomized, multicentre, placebo-controlled study", Alimentary Pharmacology & Therapeutics, vol. 26, (Jul. 30, 2007), pp. 1121-1130.

A. Mondal et al., "Coordination of motilin and ghrelin regulates the migrating motor complex of gastrointestinal motility in *Suncus murinus*", Am J Physiol Gastrointest Liver Physiol, vol. 302, (Mar. 1, 2012), pp. G1207 to G1215.

Extended European Search Report issued on Oct. 17, 2016 in Patent Application No. 14775983.1.

Betty De Smet, et al., "Motilin and ghrelin as prokinetic drug targets", Pharmacology & Therapeutics, vol. 123, No. 2, XP026337620; 2009, pp. 207-223.

F. Levin, et al., "Ghrelin Stimulates Gastric Emptying and Hunger in Normal-Weight Humans", The Journal of Clinical Endocrinology and Metabolism, vol. 91, No. 9, XP055306156, 2006, pp. 3296-3302.

J. Janssens, et al., "Improvement of Gastric Emptying in Diabetic Gastroparesis by Erythromycin", The New England Journal of Medicine, vol. 322, No. 15, XP055308354, 1990, pp. 1028-1031.

* cited by examiner

US 9,682,126 B2

POSTPRANDIAL GASTROKINETIC AGENT

TECHNICAL FIELD

The present invention relates to a postprandial gastrokinetic agent.

BACKGROUND ART

Pathological conditions (hereinafter may be referred to simply as diseases) such as diabetic gastroparesis, postoperative gastroparesis, and functional dyspepsia are known to show suppressed postprandial gastric motility and significantly degraded ability in gastric emptying of food. As drugs for enhancing gastric emptying of food to cope with such conditions, itopride hydrochloride and mosapride citrate, for example, are known. However, whether these drugs can provide sufficient effect on patients with severe conditions is still unknown. Accordingly, development of a truly effective drug is demanded.

Ghrelin is a peptide found in the stomach, and predominantly produced by gastric endocrine cells. Ghrelin is known as an appetite-stimulating peptide related to enhanced appetite and an increase in body weight. Regarding the gastric emptying of food by ghrelin, a report describes that continuous intravenous administration of ghrelin or massive administration of ghrelin to healthy subjects and patients with diabetes, both after food intake, accelerates gastric emptying (Non-Patent Documents 1 and 2). Also, administration of TZP-102, a ghrelin agonist, to fasting subjects does not accelerate gastric emptying (Non-Patent Document 3).

Motilin is a peptide of 22 amino acid residues, and is known as a substance that causes interdigestive gastric contractions in conscious dogs and humans. Motilin, when continuously administered intravenously to fasting subjects, is known to accelerate gastric emptying (Non-Patent Document 4). There is also a report describing that administration of mitemcinal, a motilin agonist, to fasting subjects enhances gastric emptying (Non-Patent Document 5).

Recently, an in vitro study was performed to investigate the gastric contractions inducing mechanism of ghrelin using an isolated stomach of *Suncus murinus*. The study revealed that administration of ghrelin alone, even at a high dose, does not accelerate gastric contractions, but treatment of subjects with a low dose of motilin in advance recovers susceptibility of ghrelin, suggesting that prior administration of motilin may open the gate of ghrelin circuit (Non-Patent Document 6).

CITATION LIST

Non-Patent Documents

Non-Patent Document 1: Neurogastroenterol. Motil. 2010, 22, e192-e200
Non-Patent Document 2: Peptides 2006, 1603-1606
Non-Patent Document 3: Neurogastroenterol. Motil. 2013, 25, e140-e150
Non-Patent Document 4: Gastroenterology. 1992, 102, 97-101
Non-Patent Document 5: Aliment Pharmacol. Ther. 2007, 26, 1121-1130
Non-Patent Document 6: Am. J. Physiol. Gastrointest. Liver Physiol. 2012, 302: G1207-G1215

SUMMARY OF THE INVENTION

Problems to be Solved by the Invention

The present invention provides a novel postprandial gastrokinetic agent.

Means for Solving the Problems

The present inventors have widely studied gastric emptying of food after food intake, not in a fasted state. It had been thought that motilin would not cause gastric contractions unless administered to subjects in a fasted state, based on the understanding that it is a causal substance of interdigestive gastric contractions. However, surprisingly, the inventors have found that when ghrelin and motilin are both administered so as to act after food intake, excellent gastric motility enhancing effect is obtained even at such low doses that ghrelin and motilin each independently does not act. The inventors have further found that ghrelin stimulates migrating motor complex (MMC) via the vagus nerve, which is indispensable for the onset of postprandial gastric contractions, and postprandial gastric contractions induced by motilin depends on the vagus nerve. The present invention has been completed based on these findings.

Specifically, the present invention provides the following [1] to [12].

[1] A postprandial gastrokinetic agent comprising (A) ghrelin or a ghrelin agonist and (B) motilin or a motilin agonist as active ingredients, wherein both the ingredients (A) and (B) are administered so as to act on the stomach after food intake.

[2] The postprandial gastrokinetic agent according to [1], wherein the administration so as to act on the stomach after food intake is administration so as to achieve effective blood levels of the ingredients (A) and (B) after food intake.

[3] The postprandial gastrokinetic agent according to [1] or [2] for a disease selected from the group consisting of diabetic gastroparesis, postoperative gastroparesis, and functional dyspepsia.

[4] A method for enhancing postprandial gastric motility, comprising administering both (A) ghrelin or a ghrelin agonist and (B) motilin or a motilin agonist so as to act on the stomach after food intake.

[5] The method for enhancing postprandial gastric motility according to [4], wherein the administration so as to act on the stomach after food intake is administration so as to achieve effective blood levels of the ingredients (A) and (B) after food intake.

[6] The method for enhancing postprandial gastric motility according to [4] or [5] for a disease selected from the group consisting of diabetic gastroparesis, postoperative gastroparesis, and functional dyspepsia.

[7] A combination of (A) ghrelin or a ghrelin agonist and (B) motilin or a motilin agonist for use in enhancing postprandial gastric motility, wherein both the ingredients (A) and (B) are administered so as to act on the stomach after food intake.

[8] The combination of the ingredients (A) and (B) according to [7], wherein the administration so as to act on the stomach after food intake is administration so as to achieve effective blood levels of the ingredients (A) and (B) after food intake.

[9] The combination of the ingredients (A) and (B) according to [7] or [8], wherein the ingredients (A) and (B) are used in a postprandial gastrokinetic agent for a disease selected from the group consisting of diabetic gastroparesis, postoperative gastroparesis, and functional dyspepsia.

[10] Use of a combination of (A) ghrelin or a ghrelin agonist and (B) motilin or a motilin agonist for production of a postprandial gastrokinetic agent, wherein both the ingredients (A) and (B) are administered so as to act on the stomach after food intake.

[11] The use according to [10], wherein the administration so as to act on the stomach after food intake is administration so as to achieve effective blood levels of the ingredients (A) and (B) after food intake.

[12] The use according to [10] or [11] for production of a postprandial gastrokinetic agent for a disease selected from the group consisting of diabetic gastroparesis, postoperative gastroparesis, and functional dyspepsia.

Effects of the Invention

According to the present invention, both (A) ghrelin or a ghrelin agonist and (B) motilin or a motilin agonist are administered so as to act on the stomach after food intake, thereby providing excellent effect of enhancing postprandial gastric motility. This can alleviate eating disorder and various postprandial symptoms in diabetic gastroparesis, postoperative gastroparesis, functional dyspepsia, and similar conditions. The effects of the present invention cannot be expected from conventionally accepted common knowledge in which motilin or a motilin agonist acts during the interdigestive period.

MODES FOR CARRYING OUT THE INVENTION

Figure 1:
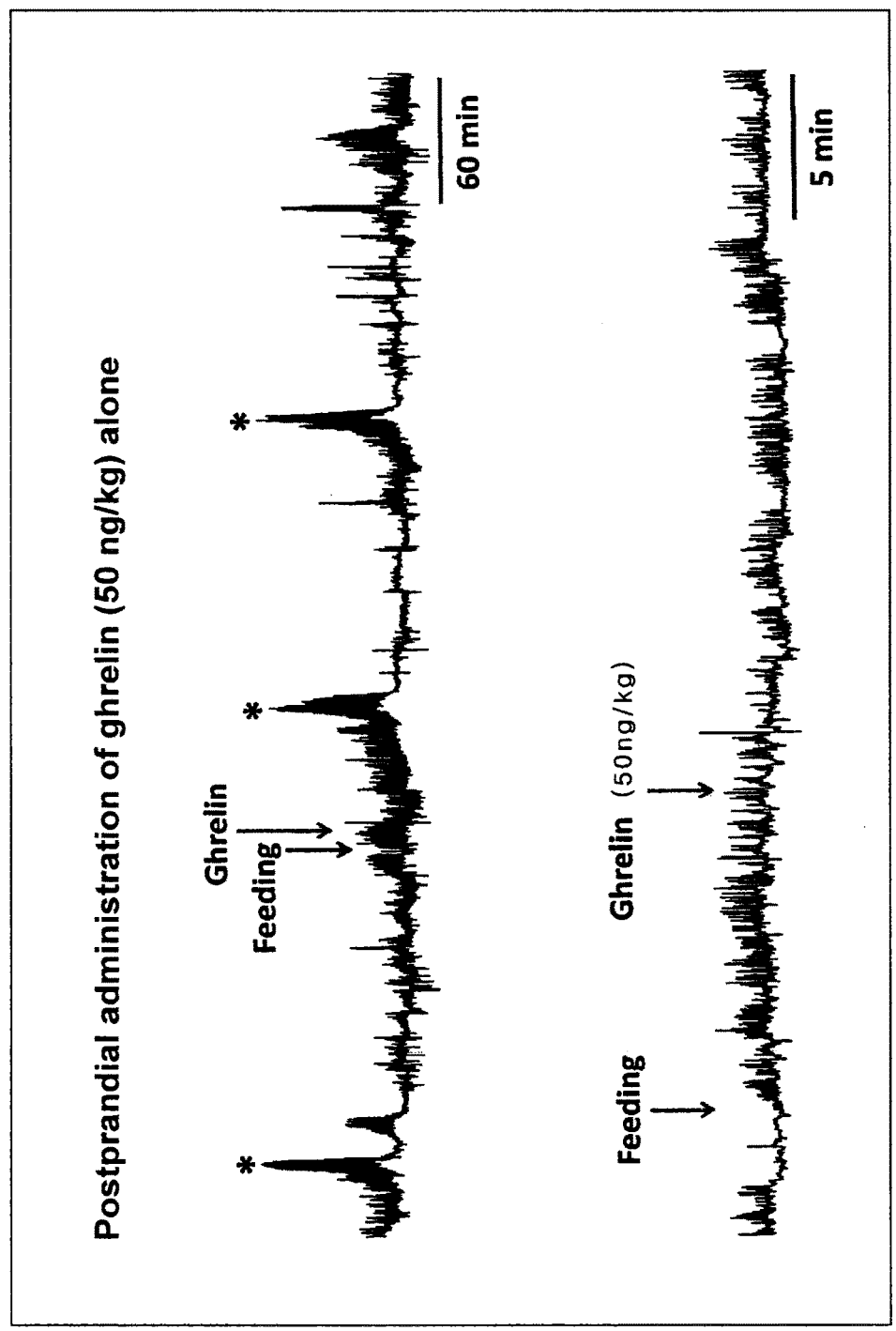
FIG. 1 is a chart showing the effect of postprandial administration of ghrelin (50 ng/kg) alone.

A combination of (A) ghrelin or a ghrelin agonist and (B) motilin or a motilin agonist is used as active ingredients of a postprandial gastrokinetic agent of the present invention.

Human ghrelin is a 28-amino acid residue peptide. In active human ghrelin, a hydroxyl group of serine at position 3 is esterified by octanoic acid. A ghrelin agonist has high selectivity to a ghrelin receptor, and is an agonist to the ghrelin receptor having an agonistic activity that is about 10 times to about 1/100 times the activity of ghrelin. Examples thereof include a cyclic peptide compound and a peptide compound. Examples of the cyclic peptide compound include TZP-102 and TZP-101. Examples of the peptide compound include anamorelin, ipamorelin, tabimorelin, capromorelin, macimorelin, CP-464709-18, EX-1314, GTP-200, MK-0677, BMS-317180, and compounds described in WO2009/098901.

Examples of the cyclic peptide compound as a ghrelin agonist include a compound represented by the following formula (1) and a salt thereof:

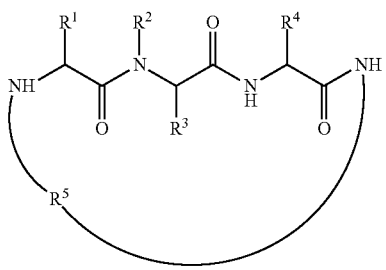

(1)

wherein $R^1$, $R^3$, and $R^4$ each independently an alkyl group, a cycloalkyl group, an arylalkyl group which may have a substituent, an aryl group, or a heterocyclic group; $R^2$ represents a hydrogen atom or an alkyl group; and $R^5$ represents an alkylene group, an alkyl-O-alkyl group, an alkyl-O-arylene group, or an alkyl-O-arylene-alkyl group.

Groups represented by $R^1$, $R^3$, and $R^4$ are preferably a linear or branched $C_1$ to $C_6$ alkyl group, a $C_3$ to $C_7$ cycloalkyl group, a phenyl-$C_{1-6}$ alkyl group (which may be substituted by halogen, $C_{1-6}$ alkoxy, $C_{1-6}$ alkyl, etc.), a $C_6$ to $C_{10}$ aryl group, an indolyl group, or an imidazolyl group. $R^2$ is preferably a $C_1$ to $C_6$ alkyl group. $R^5$ is preferably a linear or branched $C_5$ to $C_8$ alkylene group, a $C_2$ to $C_6$ alkyl-O—$C_2$ to $C_6$ alkyl group, a $C_2$ to $C_6$ alkyl-O-phenylene group, or a $C_2$ to $C_6$ alkyl-O-phenylene-$C_2$ to $C_6$ alkyl group. Herein, alkyl and alkylene may be branched.

Examples of the peptide compound as a ghrelin agonist include a compound represented by the following formula (2) or (3) and a salt thereof:

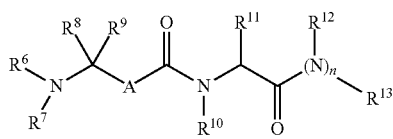

(2)

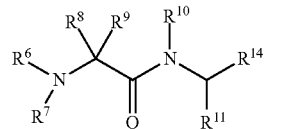

(3)

wherein $R^6$ and $R^7$ are the same or different from each other, and each independently a hydrogen atom or a $C_1$ to $C_6$ alkyl group;
$R^8$ and $R^9$ are the same or different from each other, and each independently a hydrogen atom, or a linear, branched, or cyclic $C_1$ to $C_6$ alkyl group (the alkyl group may be substituted by a halogen atom, a hydroxyl group, a $C_1$ to $C_6$ alkoxy group, a phenyl group, a benzyloxy group, or a hydroxyphenyl group), or $R^8$ or $R^9$ and $R^6$ or $R^7$ may form, together with the adjacent nitrogen atom, a pyrrolidine ring or a piperidine ring (the pyrrolidine ring or the piperidine ring may be substituted by a hydroxyl group);
$R^{10}$ and $R^{12}$ are the same or different from each other, and each independently a hydrogen atom or a methyl group;
$R^{11}$ represents a $C_1$ to $C_6$ alkyl group (the alkyl group may be substituted by a methylthio group or a benxyloxy group), a phenyl group, a phenyl-$C_{1-4}$ alkyl group, a naphthyl-$C_{1-4}$ alkyl group, or an indolyl $C_{1-4}$ alkyl group (the phenyl group or the indolyl group may be substituted by one to four groups selected from the group consisting of a $C_1$ to $C_6$ alkyl group, a halogen atom, a hydroxyl group, and a $C_1$ to $C_6$ alkoxy group);
n is a number of 0 or 1;
A represents a single bond, a $C_1$ to $C_4$ alkylene group, or a $C_2$ to $C_4$ alkenylene group; $R^{13}$ represents a formula (a), (b), or (c); and
$R^{14}$ represents the formula (c):

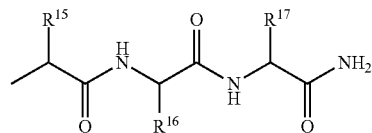

(a)

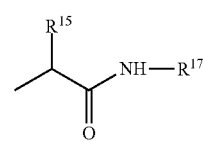

(b)

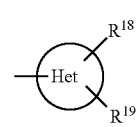

(c)

in the formulae (a) and (b), $R^{15}$ and $R^{16}$ are the same or different from each other, and each independently a phenyl-$C_1$ to $C_4$ alkyl group or a naphthyl-$C_1$ to $C_4$ alkyl group;
$R^{17}$ represents a hydrogen atom, a linear or branched $C_1$ to $C_6$ alkyl group, or an amino-$C_1$ to $C_6$ alkyl group;
$R^{18}$ represents a hydrogen atom or —CH$_2$Ar (wherein Ar represents a phenyl group, a naphthyl group, a 5-membered or 6-membered aromatic heterocyclic group having one or two heteroatoms selected from the group consisting of S, N, and O, or a condensed aromatic heterocyclic group formed from a benzene ring and a 5-membered or 6-membered heterocyclic ring having one or two heteroatoms selected from the group consisting of S, N, and O (wherein the phenyl group, the naphthyl group, or the aromatic heterocyclic group may be substituted by 1 to 3 halogen atoms, a $C_1$ to $C_6$ alkyl group, or a $C_1$ to $C_6$ alkoxy group));
$R^{19}$ represents a hydrogen atom, a $C_1$ to $C_6$ alkyl group, a $C_1$ to $C_6$ alkylsulfonyl group (wherein the alkyl group or the alkyl group in the alkylsulfonyl group may be substituted by a group selected from the group consisting of a hydroxyl group, a hydroxyalkyl carbamate group, a halogen atom, and a carbamoylalkyl carbamate group), or

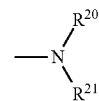

wherein $R^{20}$ and $R^{21}$ are the same or different from each other, each independently a hydrogen atom, a $C_1$ to $C_6$ alkyl group, a formyl group, or a $C_2$ to $C_6$ alkanoyl group which may be substituted by 1 to 3 halogen atoms; or $R^{20}$ and $R^{21}$ may form, together with the adjacent nitrogen atom, a 5-membered or 6-membered heterocyclic ring having one nitrogen atom; and a ring represented by Het represents a ring selected from the group consisting of an imidazolyl group, a tetrazolyl group, an indolyl-piperazine-spiro ring group, a pyrazolopyridine ring group, a 1,2,3,4-tetrahydroquinolin-2-one ring group, a piperidine ring group, and a triazolopyridine ring group.

The ring represented by Het is preferably the following ring:

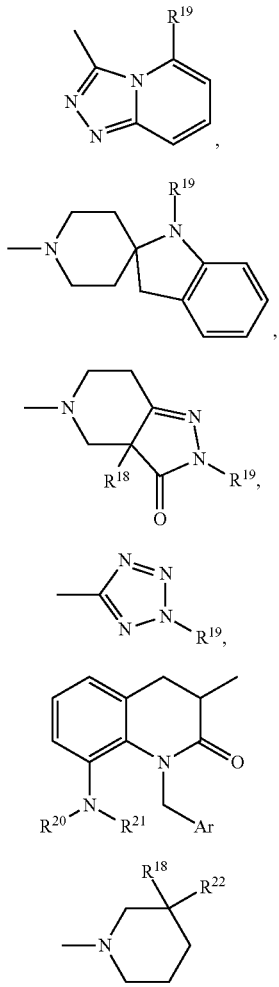

wherein $R^{22}$ represents a hydrazide group which may be substituted by 1 to 3 $C_{1-4}$ alkyl groups; and $R^{18}$ to $R^{21}$ and Ar have the same meanings as described above.

The formula (h) is preferably the following formula (h-1):

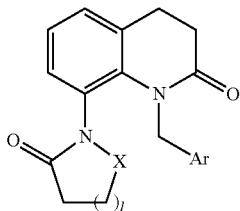

wherein X represents $CH_2$, C=O, CH—$OR^{23}$, CH—$SR^{23}$, or CH—$NR^{23}R^{24}$; l is a number of 1 or 2; $R^{23}$ and $R^{24}$ are the same or different from each other, and each independently a hydrogen atom or a linear, branched, or cyclic $C_1$ to $C_6$ alkyl group; and Ar has the same meaning as defined above.

Human motilin is a 22-amino acid residue peptide. A motilin agonist has high selectivity to a motilin receptor, and is an agonist to the motilin receptor having an agonistic activity that is about 10 times to about 1/100 times the activity of motilin. Examples thereof include a macrolide-based compound, for example, mitemcinal fumarate, erythromycin, EM-523, GSK-962040, GSK-1322888, ABT-229, atilmotin, RQ-00201894, SK-896, and idremcinal.

Examples of an erythromycin derivative as a motilin agonist include a compound represented by the following formula (4):

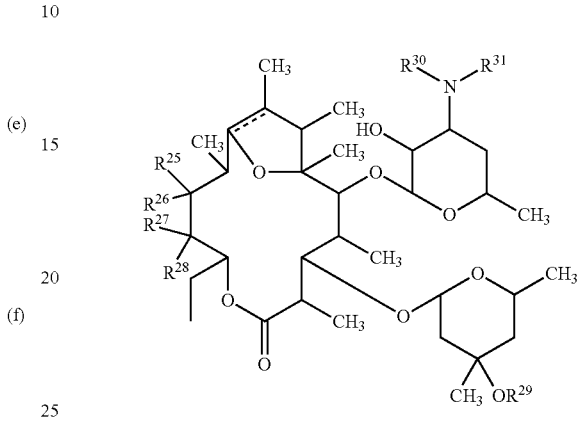

wherein $R^{25}$ and $R^{26}$ each independently a hydrogen atom, a hydroxy group, or a methyl group, or $R^{25}$ and $R^{26}$ together form an oxo group;
$R^{27}$ and $R^{28}$ each independently a hydrogen atom, a hydroxy group, or a methyl group;
$R^{29}$ represents a hydrogen atom or a methyl group;
$R^{30}$ and $R^{31}$ each independently a $C_1$ to $C_4$ alkyl group; and a dotted line may be a double bond.

The present invention is characterized in that both the ingredients (A) and (B) are administered so as to act on the stomach after food intake. The ingredient (A) is generally known to enhance gastric emptying of food under administration after food intake. The ingredient (B) is known to act only on an empty stomach. However, administration of both the ingredients (A) and (B) after food intake can achieve excellent effect of enhancing gastric motility even in such doses that the ingredients (A) and (B) each independently do not enhance gastric motility, as described in Examples below.

Herein, the administration of the ingredients (A) and (B) so as to act on the stomach after food intake means that the ingredients (A) and (B) are administered so as to exert actions of the ingredients (A) and (B) after food intake, that is, after food is taken into the stomach. For example, the ingredients (A) and (B) are administered so as to achieve effective blood levels of the ingredients (A) and (B) after food intake. A time required for achieving the effective blood level varies depending on the route of administration. For oral administration, the time is about 20 minutes to about 60 minutes after the administration, and for intravenous administration, the time is within about 10 minutes after the administration. Thus, both the ingredients (A) and (B) may be administered so as to achieve the effective blood levels after food intake in consideration of the route of administration.

In the present invention, "after food intake" means within about 30 minutes immediately after intake of a meal.

When the ingredients (A) and (B) are administered by the same route, the ingredients (A) and (B) may be administered simultaneously. When the ingredients (A) and (B) are administered by different routes, the timings of administration vary. For example, when the ingredient (A) is a preparation for oral administration and the ingredient (B) is a preparation for intravenous administration, it is desired that the ingredient (A) be administered from about 30 minutes before to immediately before intake of a meal and the ingredient (B) be administered immediately after food intake.

In the present invention, the ingredients (A) and (B) may be contained in one preparation, or each contained in different preparations. A preparation containing the ingredient (A) and a preparation containing the ingredient (B) may be different in the route of administration. The preparation containing the ingredient (A) and the preparation containing the ingredient (B) may be sold in a form of combination preparation (kit).

The mode of administration of pharmaceutical of the present invention is not particularly limited, and can be selected properly according to the therapeutic purpose. Specific examples thereof include an oral preparation (tablet, coating tablet, powder, granule, capsule, solution, etc.), an injection, a suppository, a patch, and an ointment. For ghrelin and motilin, an injection is preferred, and for a ghrelin agonist and a motilin agonist, an oral preparation and an injection are preferred.

The pharmaceutical of the present invention can be prepared using a pharmaceutically acceptable carrier depending on the mode of administration by a generally known method. Examples of the carrier include various agents generally used for a drug. Specific examples thereof include an excipient, a binder, a disintegrant, a lubricant, a diluent, a solution adjuvant, a suspending agent, a tonicity agent, a pH adjuster, a buffer, a stabiliser, a colorant, a flavoring agent, and a smell masking agent.

In the present invention, each dose of the ingredients (A) and (B) may be lower than the dose at which each of the ingredients (A) and (B) is predicted to independently act. It is sufficient that the dose of the ingredient (A) be, for example, $1/50$ to $1/500$ of the dose at which the ingredient (A) is usually predicted to act alone. It is sufficient that the dose of the ingredient (B) be, for example, $1/3$ to $1/30$ of the dose at which the ingredient (B) is usually predicted to act alone.

In the present invention, the dose of ghrelin is preferably 1.5 to 20 mg, more preferably 2 to 6 mg per intravenous administration per adult. The dose of motilin is preferably 6 to 40 mg, more preferably 9 to 20 mg per intravenous administration per adult. The doses of ghrelin agonist and motilin agonist vary depending on the route of administration and an ingredient, and can be determined in accordance with ghrelin-like action and motilin-like action of the agonists in consideration of the doses of ghrelin and motiolin.

The present invention can enhance postprandial gastric motility, and thus promote postprandial gastric emptying of food. Accordingly, the present invention can alleviate a symptom of decreasing gastric emptying of food due to diabetic gastroparesis, postoperative gastroparesis, and functional dyspepsia.

EXAMPLES

The present invention will be described below in detail with reference to Examples.

Example 1

Effects of administration of each of ghrelin and motilin and co-administration of ghrelin and motilin on postprandial gastric motility in *Suncus murinus* were studied.

(1) Material and Method

A. Drug

Each of *Suncus* motilin (Scrum Inc., Tokyo, Japan) and human ghrelin (Asubio Pharma Co., Ltd., Hyogo, Japan) was dissolved in phosphate buffered saline (PBS) containing 0.1% bovine serum albumin.

B. Animal

*Suncus murinus* (male, outbred KAT strain, 8 to 9 weeks old, 73 to 90 g) was used for the experiment. Each animal was bred in a plastic cage provided with an empty can as a nest box under the following conditions: temperature at $23\pm2°$ C., illumination between 8:00 and 20:00, and free intake of commercial trout feed (SP, Nippon Formula Feed Mfg Co., Ltd., Yokohama, Japan).

C. Operation (Fixation Suture of Force Transducer and Insertion of Catheter into Jugular Vein)

After 3 hours of fasting, *Suncus murinus* was anesthetized by an intraperitoneal injection of pentobarbital sodium (50 mg/kg). Through a midline incision, the stomach was exposed outside the body, and a force transducer was fixed via suture in the circular muscle direction of the body of stomach. The wire extending from the force transducer was inserted through the abdominal wall, passed under the skin, and exposed at the back of the neck.

An intravenous catheter was inserted in the right jugular, and extracorporeally fixed to the back. The catheter was filled with heparinized saline (100 units/mL) to prevent clotting.

Each of the operated *Suncus murinus* was allowed to recover for several days.

D. Measurement of Gastric Motility

Drug administration and measurement of gastric motility were performed in the conscious, free-moving state without anesthesia.

E. Administration 2 g of feed was given to the *Suncus murinus* fastened (for 8 to 10 hours) for 10 minutes. After the intake of feed for 10 minutes, ghrelin (50 ng/kg), motilin (300 ng/kg), or a mixed solution of ghrelin (50 ng/kg) and motilin (100, 200, or 300 ng/kg) was intravenously administered through a jugular vein catheter rapidly.

F. Measurement of Gastric Motility

Amplified analog signals were converted into digital signals by an analog-to-digital converter (ADC-20, Pico Technology Ltd, St Neots, UK), and the digital signals were recorded on a computer.

Phase III contractions of MMC in conscious *Suncus murinus* were defined on the basis of those in dogs and humans (that is, clustered contractions with an amplitude of 8 g or more that lasts for 5 minutes or more).

G. Data Analysis

Gastric motility was quantitated using a motility index (MI). A motility index (MI) based on a drug was calculated using the following equation.

$$MI (\%) = A/B \times 100$$

A: AUC of contractions for 10 minutes during which the drug was administered

B: AUC of 10-minute spontaneous phase III contractions appeared before administration of the drug H. Statistical Analysis After one-way ANOVA, a multiple comparison test was performed by the Tukey's method. A p value of 0.05 or less was considered to be statistically significant.

Figure 2:
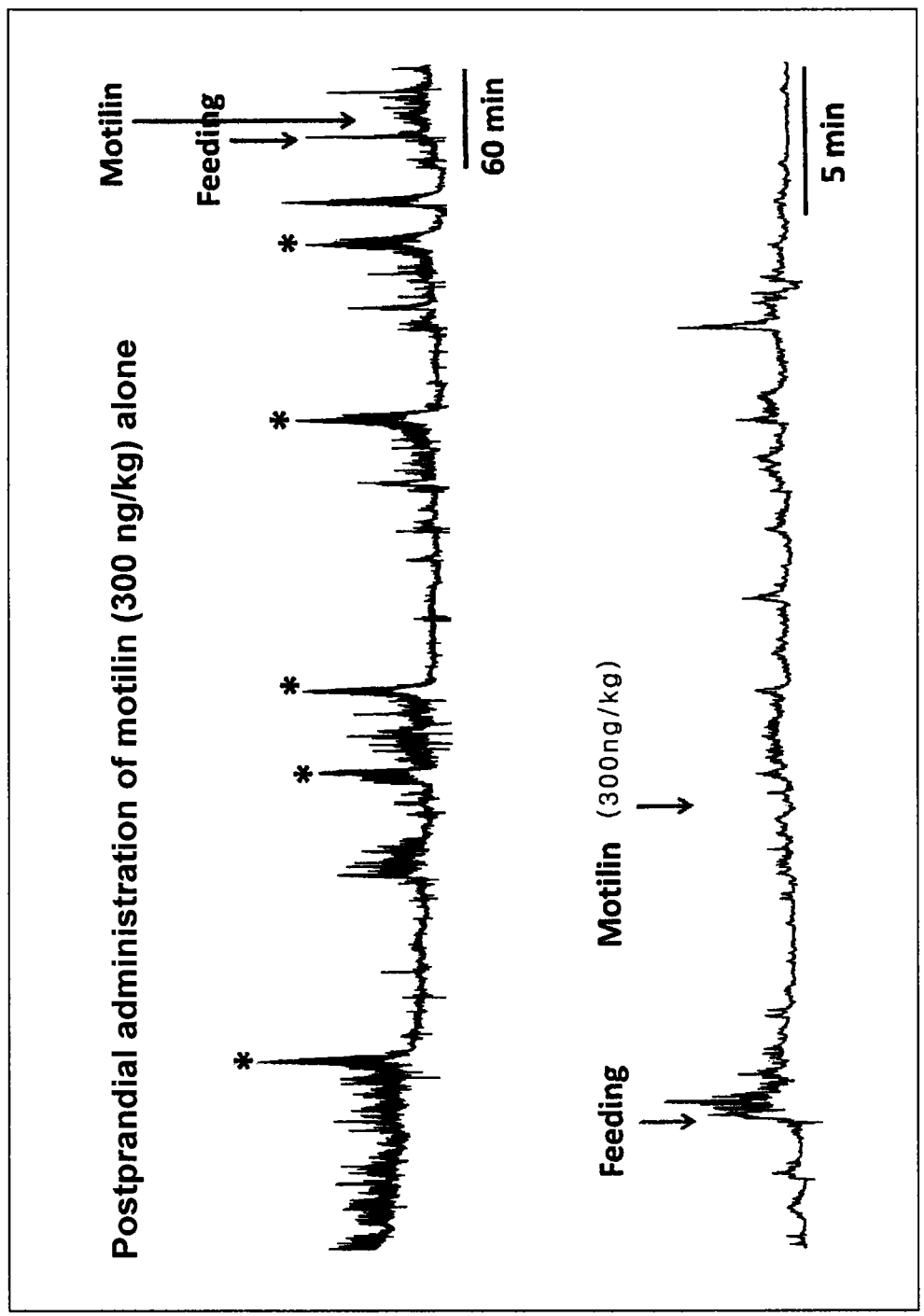
FIG. 2 is a chart showing the effect of postprandial administration of motilin (300 ng/kg) alone.
Figure 3:
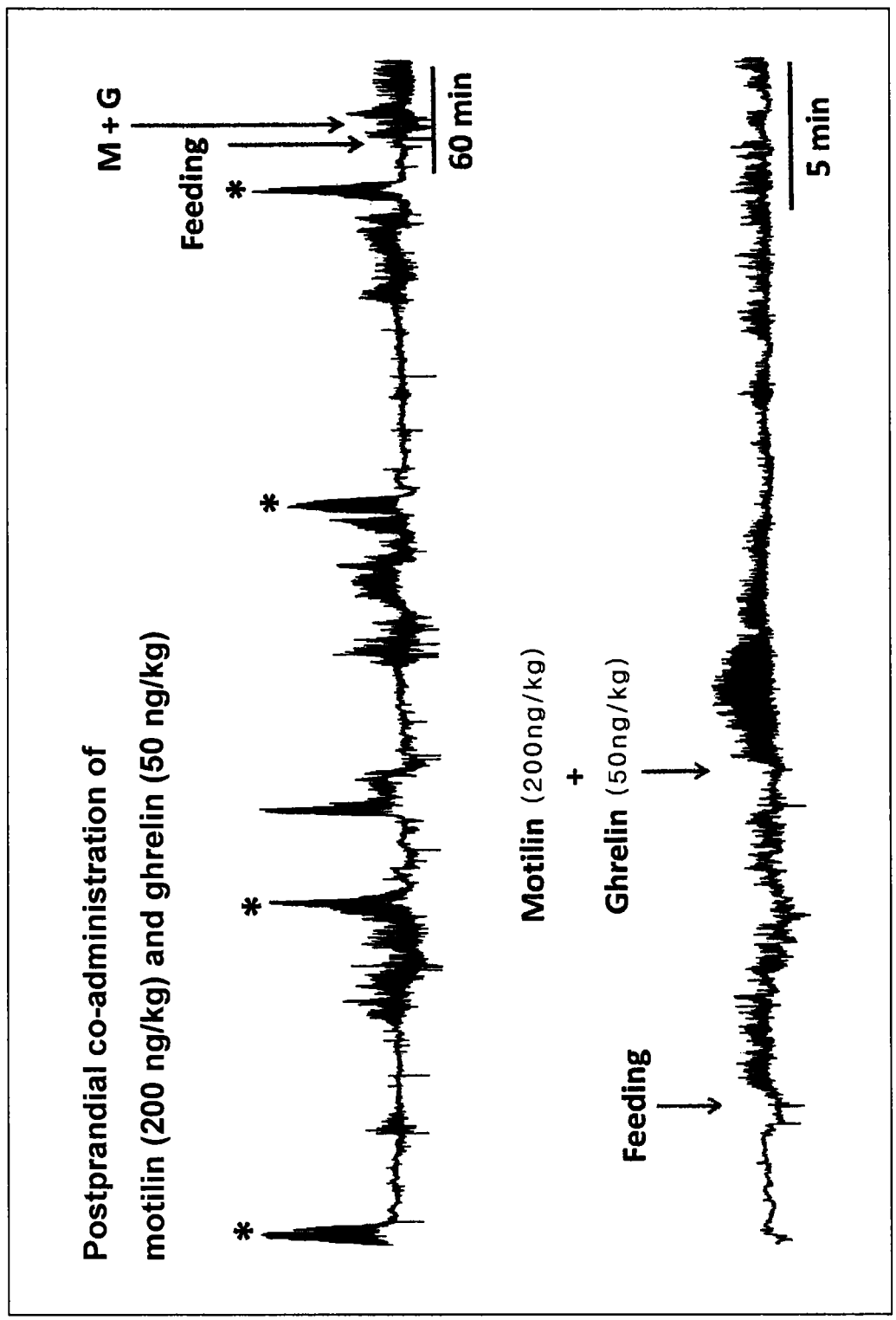
FIG. 3 is a chart showing the effect of postprandial co-administration of motilin (200 ng/kg) and ghrelin (50 ng/kg).
Figure 4:
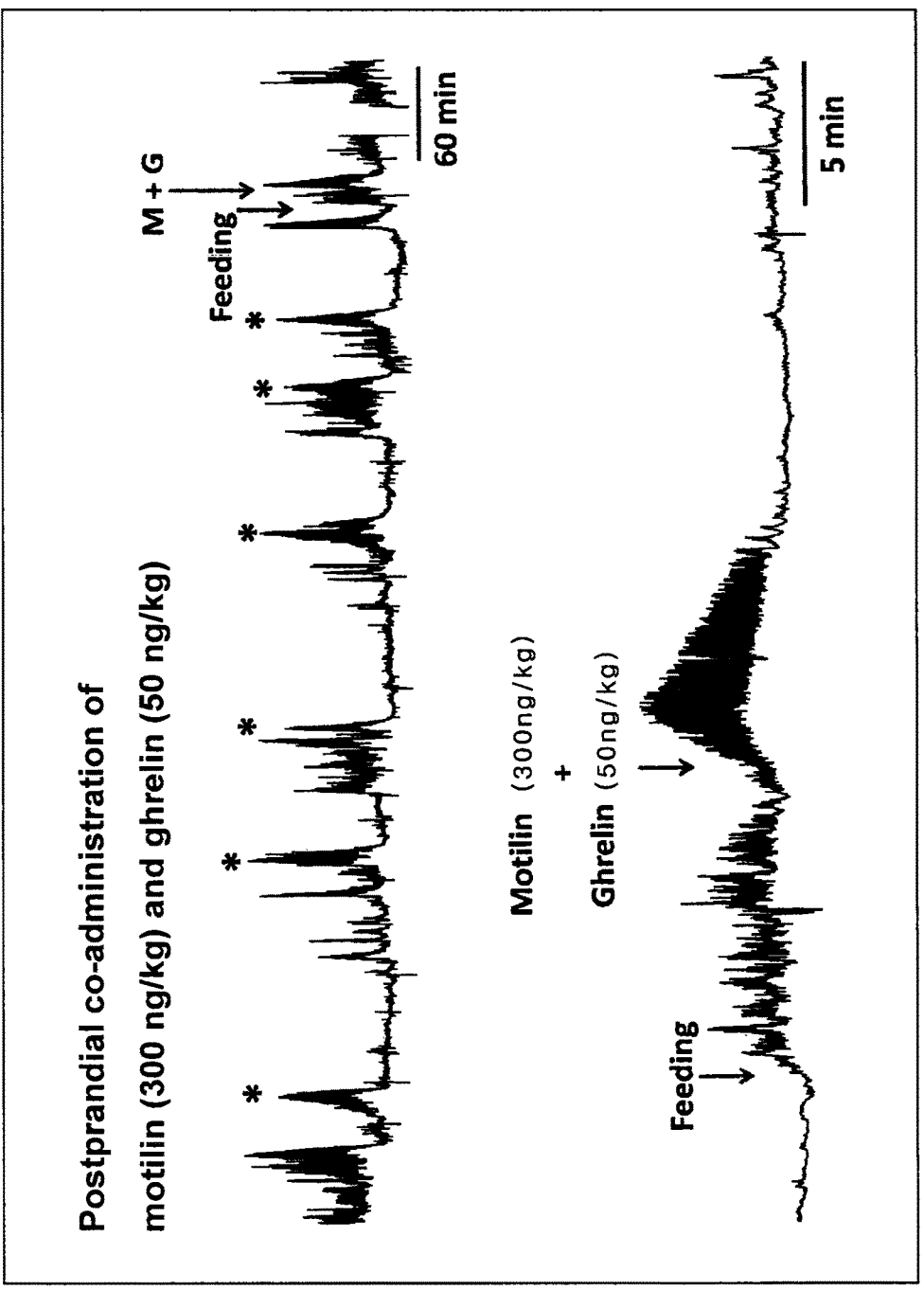
FIG. 4 is a chart showing the effect of postprandial co-administration of motilin (300 ng/kg) and ghrelin (50 ng/kg).

(2) Results
A. Action of Ghrelin Alone
50 ng/kg of ghrelin (G) did not induce contractions of the body of the stomach (FIG. 1).
B. Action of Motilin Alone
300 ng/kg of motilin (M) did not induce contractions of the body of the stomach (FIG. 2).
C. Action by Co-Administration of Ghrelin (G) and Motilin (M)
50 ng/kg of G and 200 ng/kg of M induced phase III-like contractions smaller than spontaneous phase III contractions (FIG. 3).
(Motility index: about 45%)
50 ng/kg of G and 300 ng/kg of M induced phase III-like contractions (FIG. 4).
(Motility index: about 85%)

Example 2

(1) Material and Method
A. Drug
Each of *Suncus* motilin (Scrum Inc., Tokyo, Japan) and human ghrelin (Asubio Pharma Co., Ltd., Hyogo, Japan) were dissolved in PBS containing 0.1% bovine serum albumin.
B. Animal
*Suncus murinus* (male, outbred KAT strain, 7 to 15 weeks old, 60 to 100 g) was used for the experiment. Each animal was bred in a plastic cage provided with an empty can as a nest box under the following conditions: temperature at 23±2° C., illumination between 8:00 and 20:00, and free intake of commercial trout feed (SP, Nippon Formula Feed Mfg Co., Ltd., Yokohama, Japan).
C. Operation (Fixation Suture of Force Transducer, Vagotomy, and Insertion of Catheter into Jugular Vein)
After 3 hours of fasting, *Suncus murinus* was anesthetized by an intraperitoneal injection of pentobarbital sodium (50 mg/kg). Through a midline incision, the stomach was exposed outside the body, and a force transducer was fixed via suture in the circular muscle direction of the body of stomach. The wire extending from the force transducer was inserted through the abdominal wall, passed under the skin, and exposed at the back of the neck. Thereafter, truncal vagotomy was performed. A lower portion of the esophagus was exposed, both branches of the vagus nerve were isolated, and about 3 mm of the vagus nerve was excised above the hepatic branch and the celiac branch. For sham-operated *Suncus murinus*, the vagus nerve was exposed, but not excised. An intravenous catheter was inserted in the right jugular, and extracorporeally fixed to the back. The catheter was filled with heparinized saline (100 units/mL) to prevent clotting.
From 2 days after the operation, the gastric motility was recorded.
D. Administration of Motilin and Ghrelin During Interdigestive Period and Postprandial Period Interdigestive Period
Administration of motilin was initiated 10 minutes after completion of spontaneous phase III. Synthesized *suncus* motilin was continuously injected at 50 ng/kg/min over 10 minutes, and the continuously injected amount was 50 µL/100 g BW/min. Administration of ghrelin was initiated 10 minutes after completion of spontaneous phase II. Acyl ghrelin was continuously injected at 0.1, 0.3, 1, or 3 µg/kg/min over 10 minutes.
Postprandial Period
1 g of feed was given to the *Suncus murinus* during phase I to observe postprandial contractions. Motilin was continuously injected at 50 ng/kg/min over 10 minutes 20 minutes after completion of intake of feed.
E. Measurement of Gastric Motility
Amplified analog signals were converted into digital signals by an analog-to-digital converter (ADC-20, Pico Technology Ltd, St Neots, UK), and the digital signals were recorded on a computer. Phase III contractions of MMC in conscious *Suncus murinus* were defined on the basis of those in dogs and humans (that is, clustered contractions with an amplitude of 8 g or more that lasts for 5 minutes or more).
F. Data
Gastric motility was quantitated using a motility index (MI). A motility index (MI) based on a drug was calculated using the following equation.

$$MI\ (\%) = A/B \times 100$$

A: AUC of contractions for 10 minutes during which the drug was administered
B: AUC of 10-minute spontaneous phase III contractions appeared before administration of the drug
H. Statistical analysis
After ANOVA, Student's t test was performed. A p value of 0.05 or less was considered to be statistically significant.

(2) Results

Figure 5A:
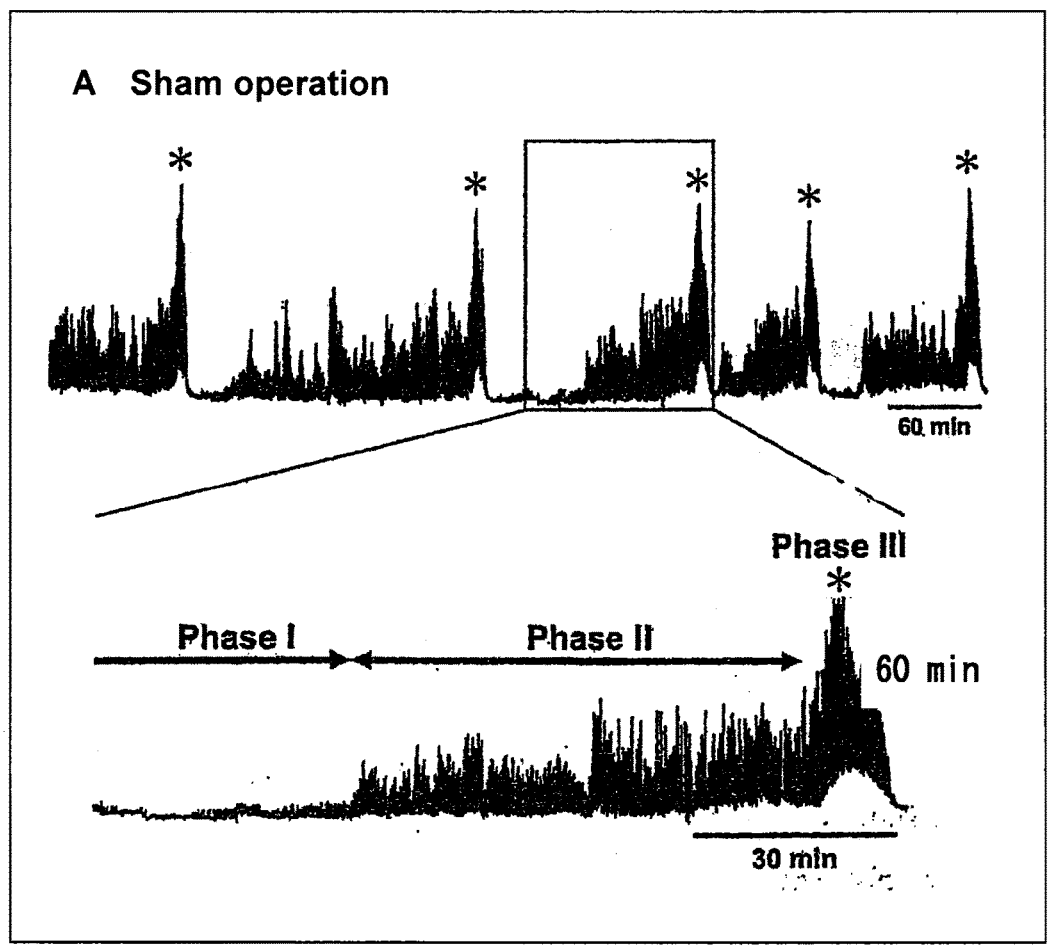
FIG. 5A is a chart showing spontaneous contractions of the stomach of sham-operated Suncus murinus in the fasted state.
Figure 5B:
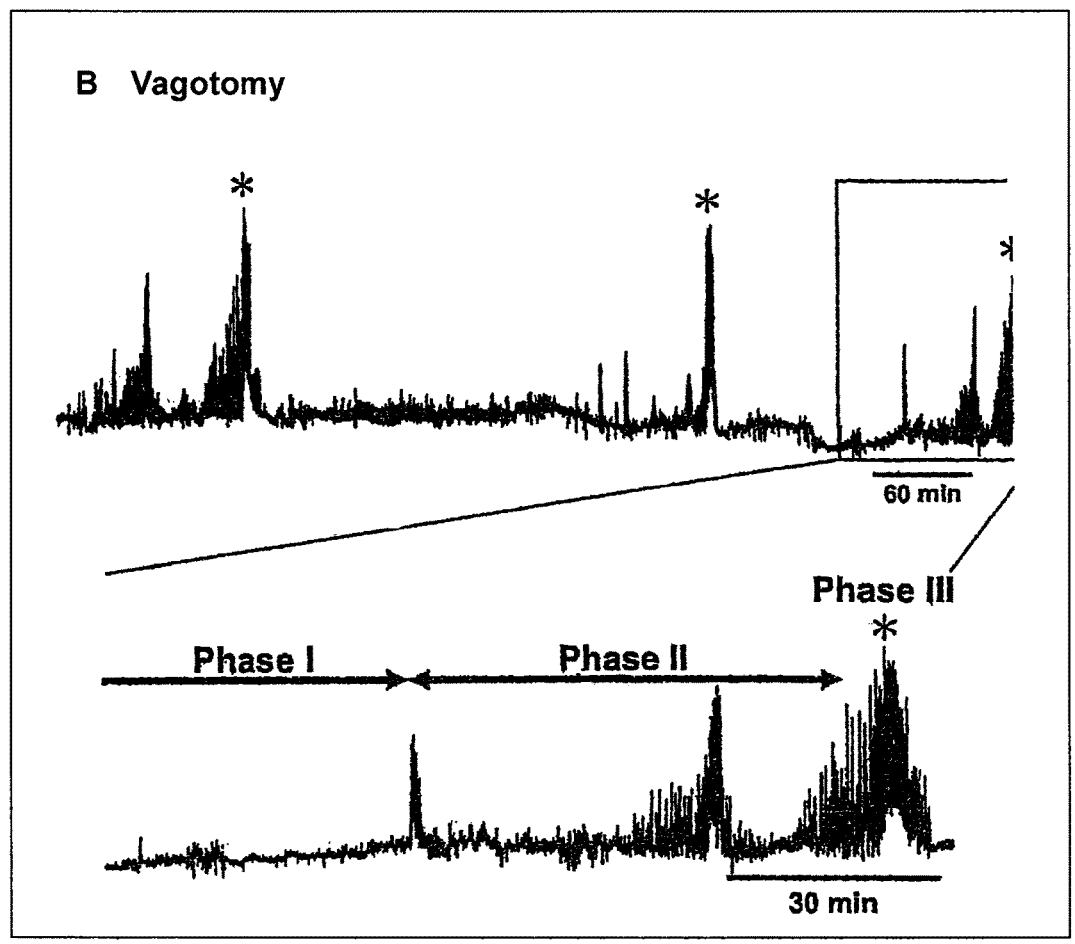
FIG. 5B is a chart showing spontaneous contractions of the stomach of vagotomized Suncus murinus in the fasted state.
Figure 5C:
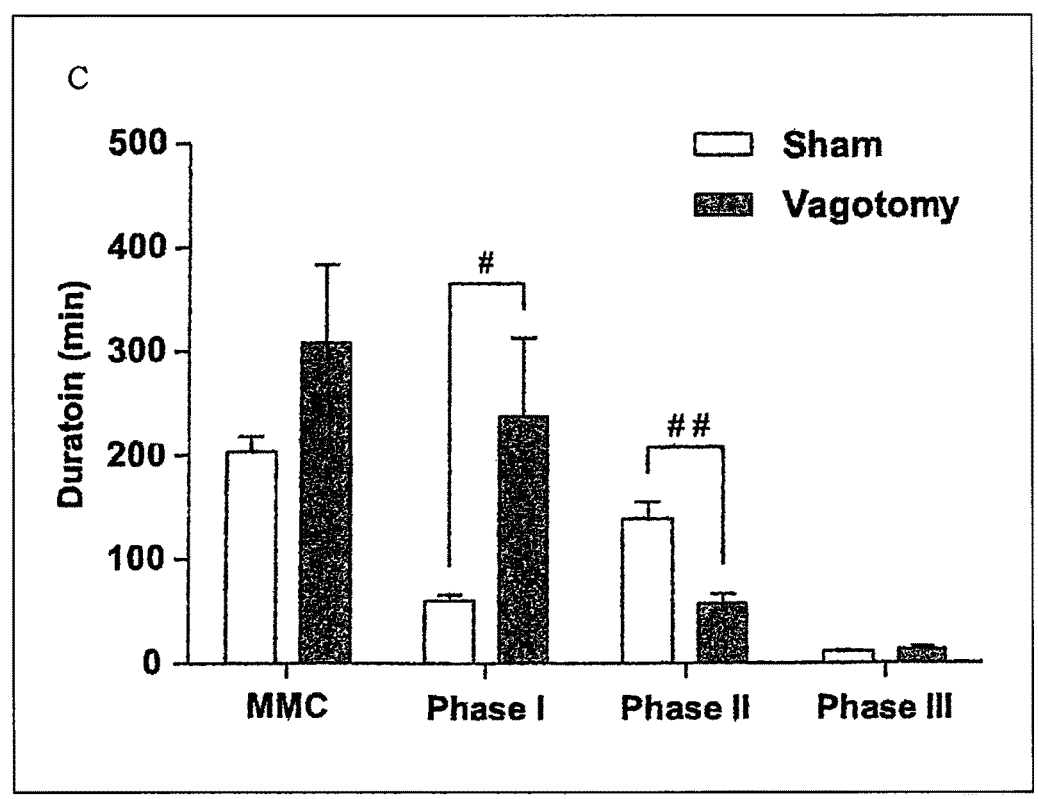
FIG. 5C is a graph showing contraction duration at each phase of MMC in the sham-operated Suncus murinus and the vagotomized Suncus murinus.
Figure 5D:
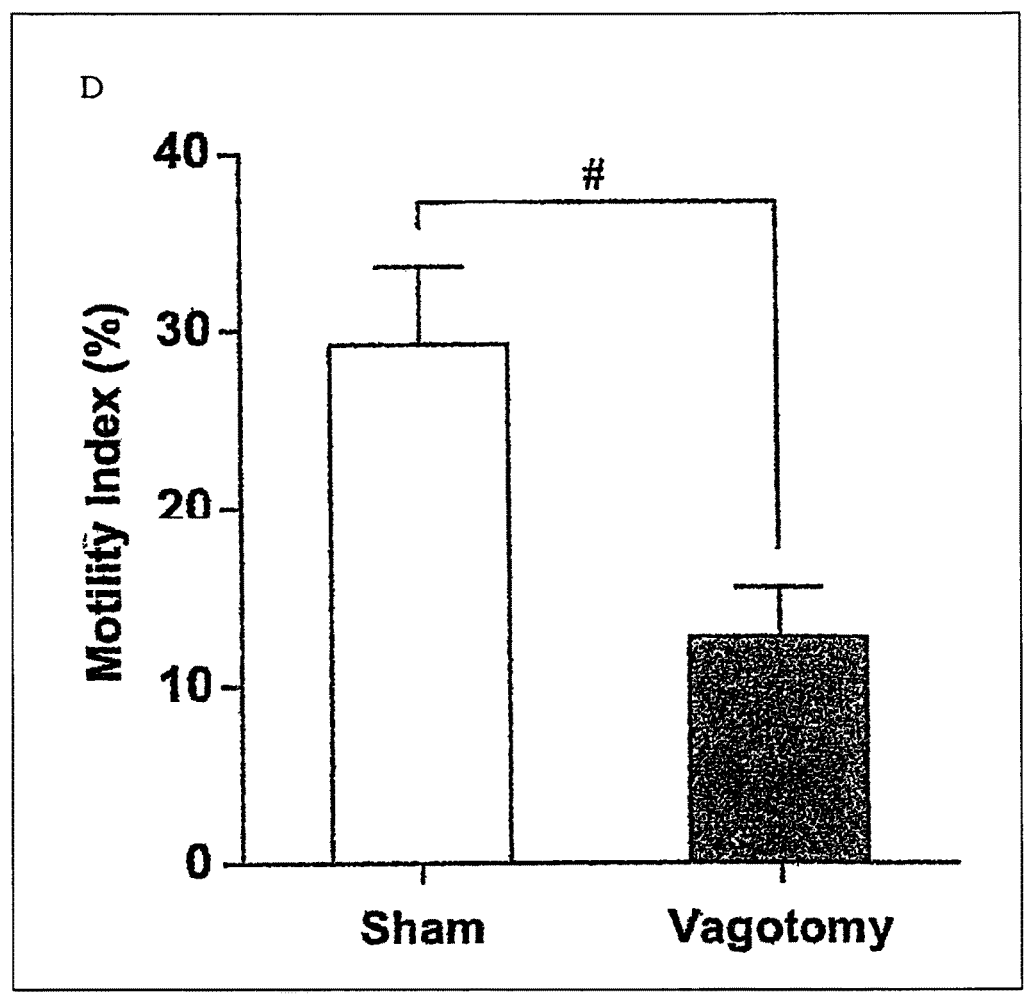
FIG. 5D is a graph showing a motility index at phase II of MMC in the sham-operated Suncus murinus and the vagotomized Suncus murinus.
Figure 6A:
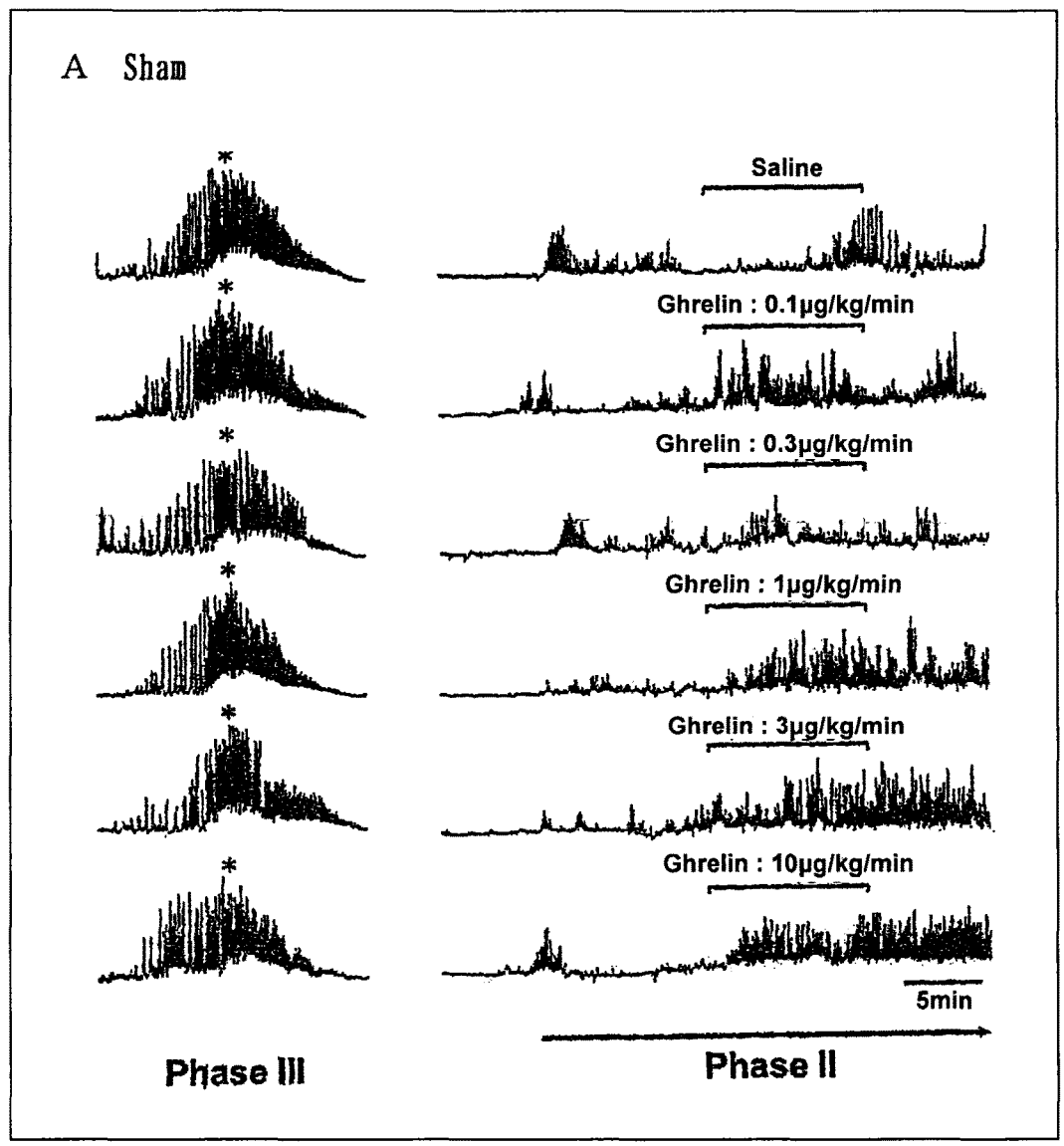
FIG. 6A is charts showing the effect of ghrelin at phase II of MMC in the the sham-operated Suncus murinus.
Figure 6B:
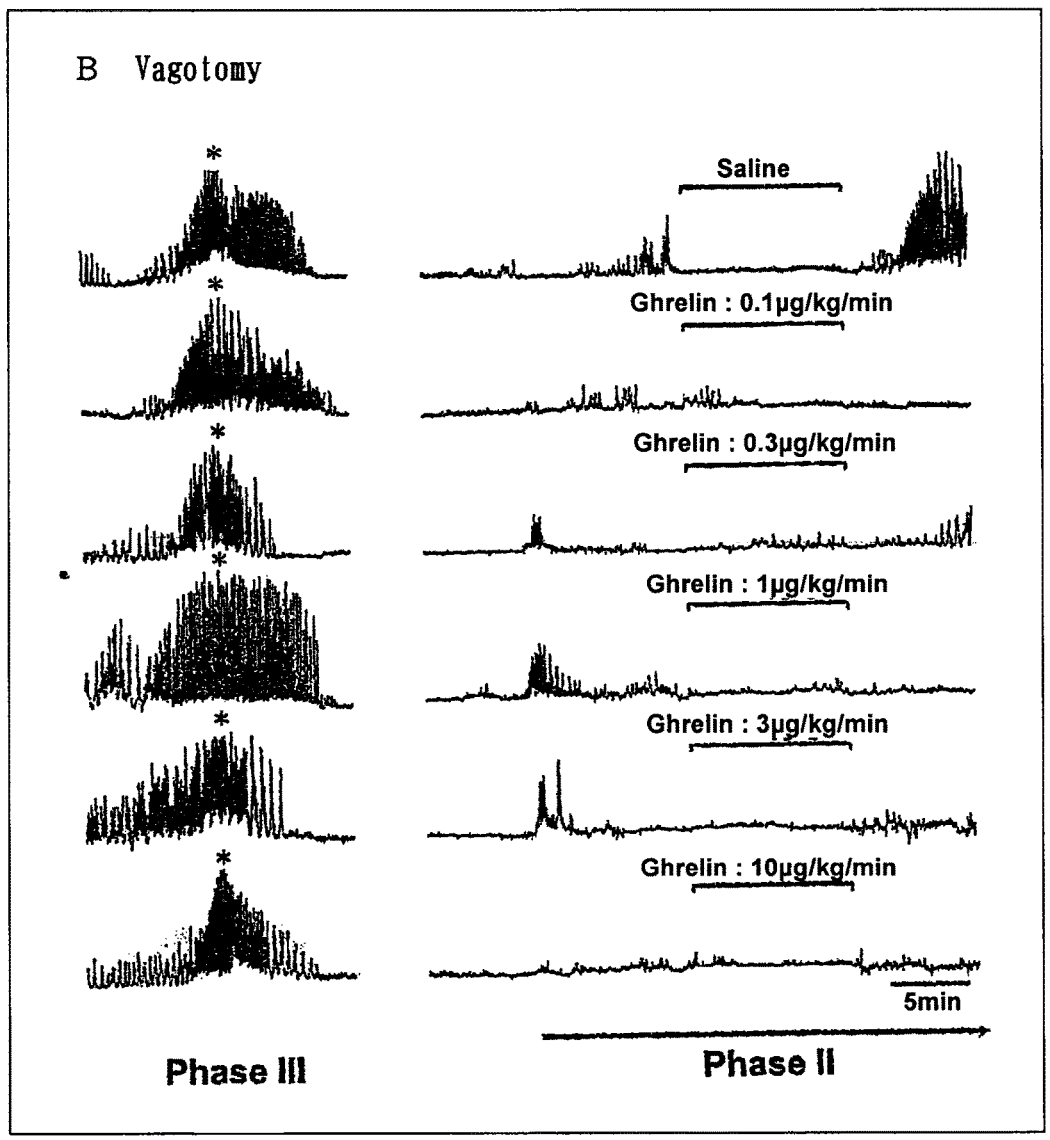
FIG. 6B is charts showing the effect of ghrelin at phase II of MMC in the the vagotomized Suncus murinus.
Figure 6C:
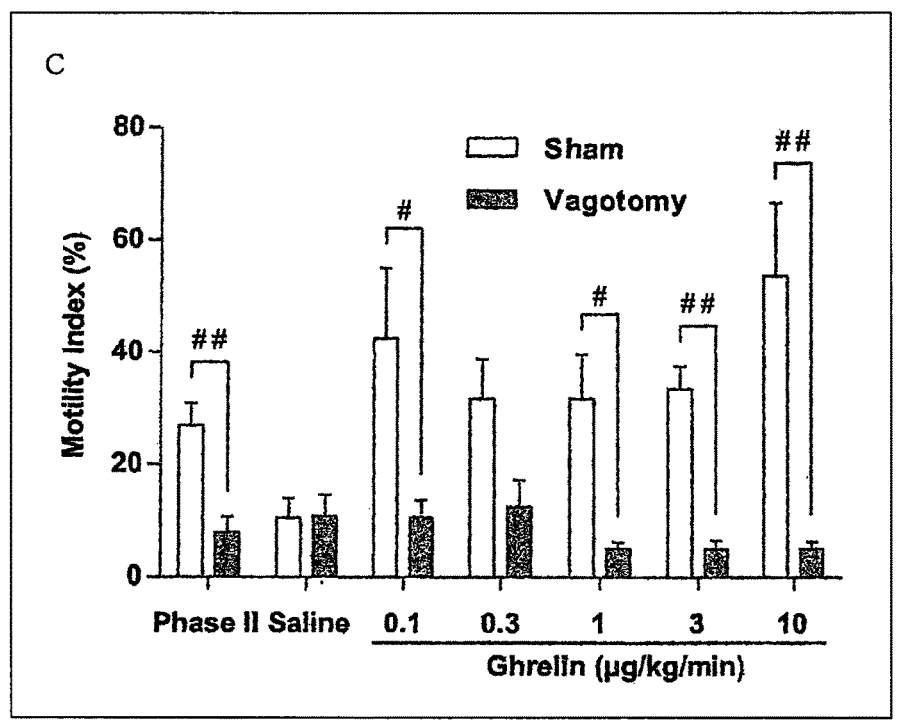
FIG. 6C is a graph showing a motility index during administration of ghrelin in the sham-operated Suncus murinus and the vagotomized Suncus murinus.
Figure 7A:
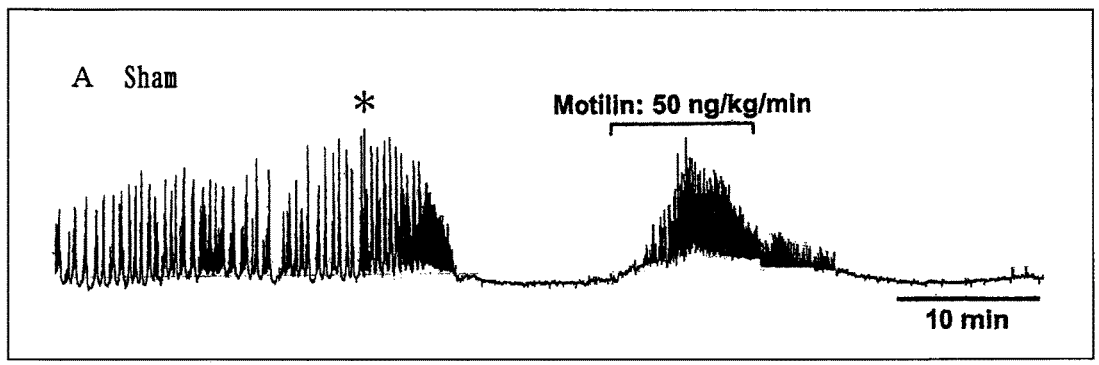
FIG. 7A is a chart showing spontaneous contractions by administration of motilin in the sham-operated Suncus murinus.
Figure 7B:
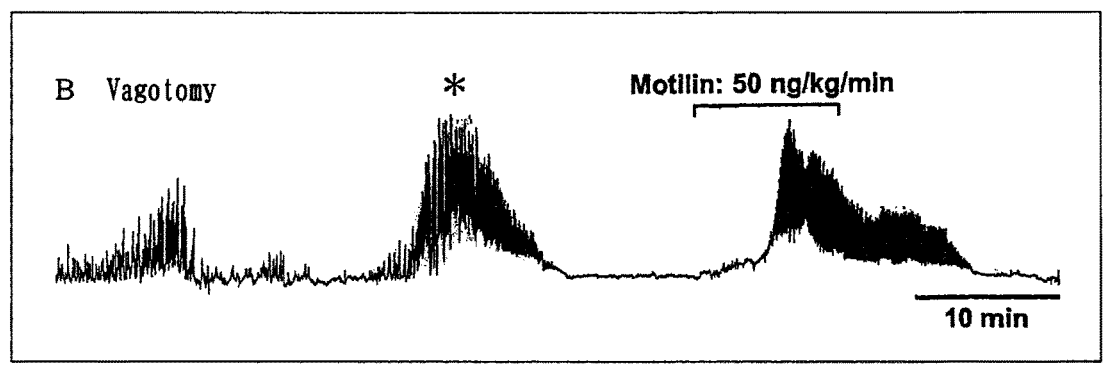
FIG. 7B is a chart showing spontaneous contractions by administration of motilin in the vagotomized Suncus murinus.
Figure 7C:
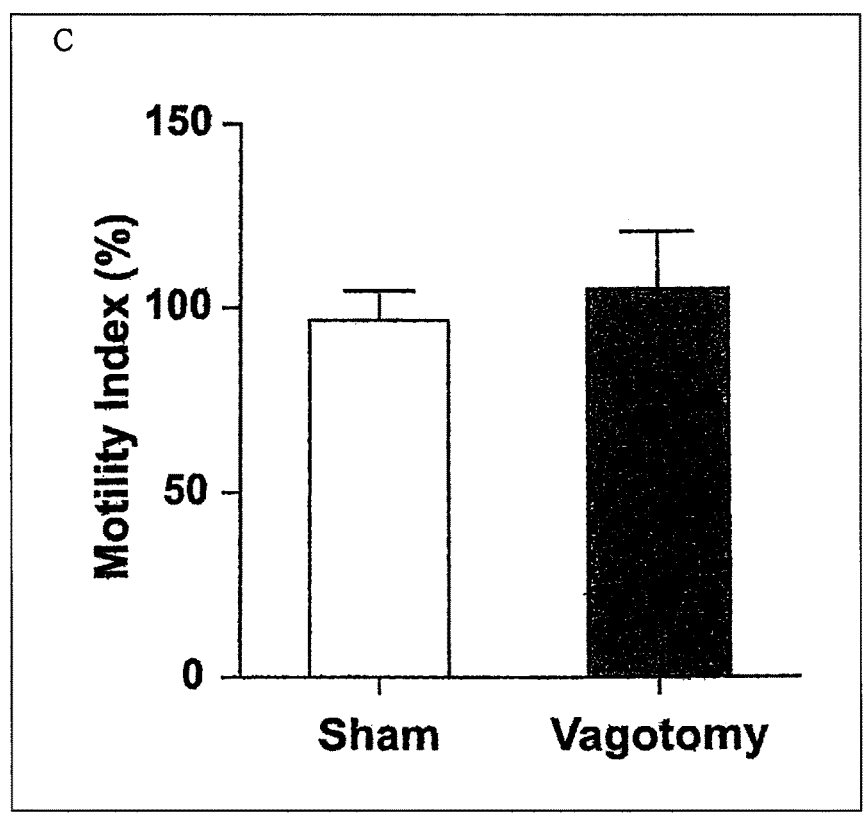
FIG. 7C is a graph showing a motility index during administration of motilin in the sham-operated Suncus murinus and the vagotomized Suncus murinus.
Figure 7D:
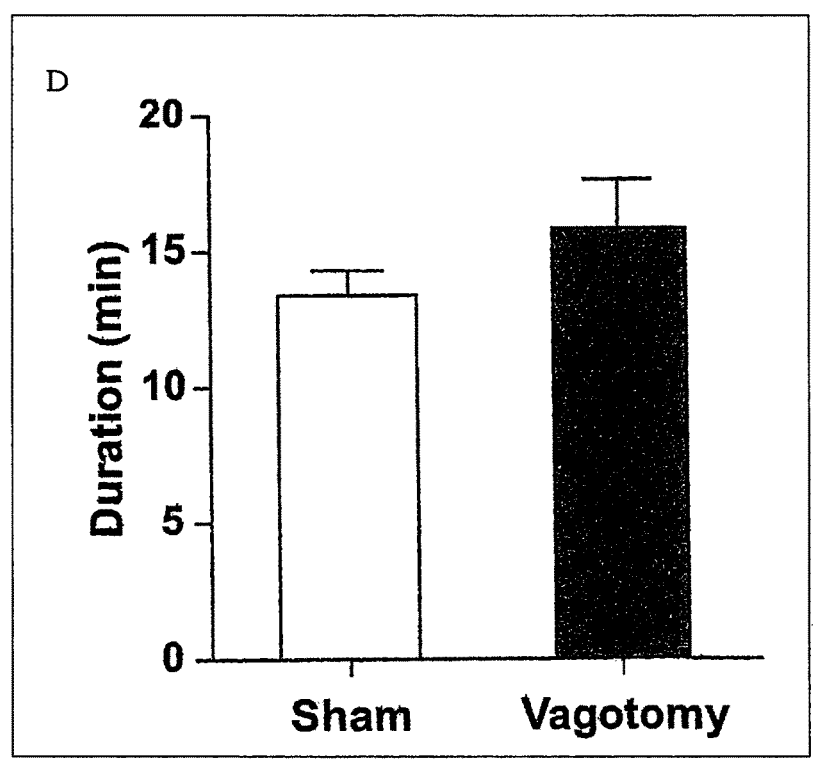
FIG. 7D is a graph showing contraction duration during administration of motilin in the sham-operated Suncus murinus and the vagotomized Suncus murinus.

A. Spontaneous Contractions in Fasting State
In both the sham-operated *Suncus murinus* and the vagotomized *Suncus murinus* in the fasted state, periodic migrating motor complex (MMC) including phases I, II, and III was visibly observed (FIGS. 5A and 5B). The period (57±9 minutes) of phase II in the vagotomized *Suncus murinus* was significantly shorter than the period (139±16 minutes) of phase II in the sham-operated *Suncus murinus*. The period of phase I in the vagotomized *Suncus murinus* increased (238±76 minutes vs 60±6 minutes). In terms of the whole period of MMC and the phase III period, there were no significant differences between the sham-operated *Suncus murinus* and the vagotomized *Suncus murinus* (FIG. 5C). The motility index (MI) (13%±3%) of phase II in the vagotomized *Suncus murinus* was significantly lower than the motility index (MI) (29%±5%) of phase II in the sham-operated *Suncus murinus* (FIG. 5D).
B. Effect of Ghrelin in Phase II of MMC
10 minutes after initiation of phase II contractions, saline or ghrelin (at 0.1, 0.3, 1, 3, or 10 µg/kg/min) was intravenously injected over 10 minutes. In the sham-operated *Suncus murinus*, ghrelin amplified the amplitude of spontaneous phase II contractions (FIG. 6A). However, ghrelin did not change the amplitude of spontaneous phase II contractions in the vagotomized *Suncus murinus* (FIG. 6B).
The MI in the sham-operated *Suncus murinus* during administration of ghrelin was higher than the MI in the vagotomized *Suncus murinus* during administration of ghrelin (FIG. 6C).
C. Effect of Motilin in Phase I of MMC
10 minutes after spontaneous phase III contractions, motilin (at 50 ng/kg/min) was intravenously injected over 10 minutes. In both the sham-operated *Suncus murinus* and the vagotomized *Suncus murinus*, motilin-induced phase III-like contractions were observed (FIGS. 7A and 7B). In the motility index (MI) during administration of motilin and the contraction duration due to motilin, a significant difference was not observed (FIGS. 7C and 7D).

D. Postprandial Gastric Motility and Effect of Motilin in Postprandial State

Figure 8A:
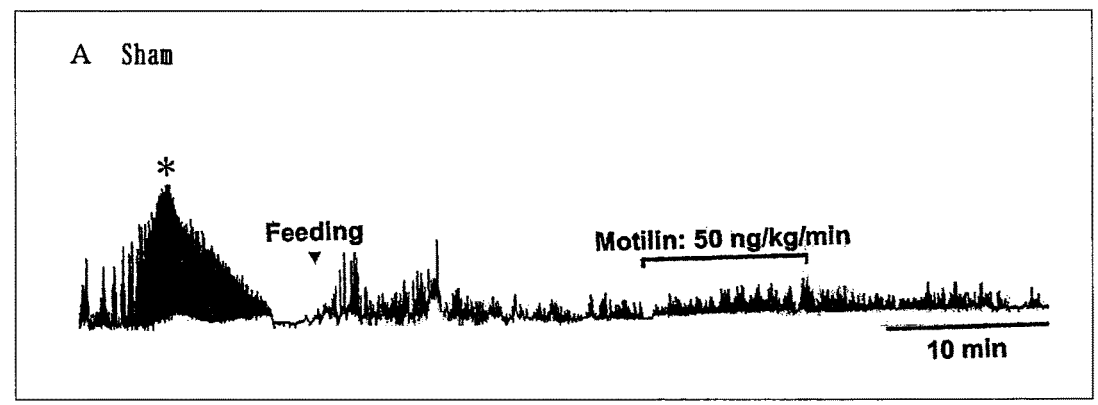
FIG. 8A is a chart showing an action for gastric contractions by administration of motilin after food intake in the sham-operated Suncus murinus.
Figure 8B:
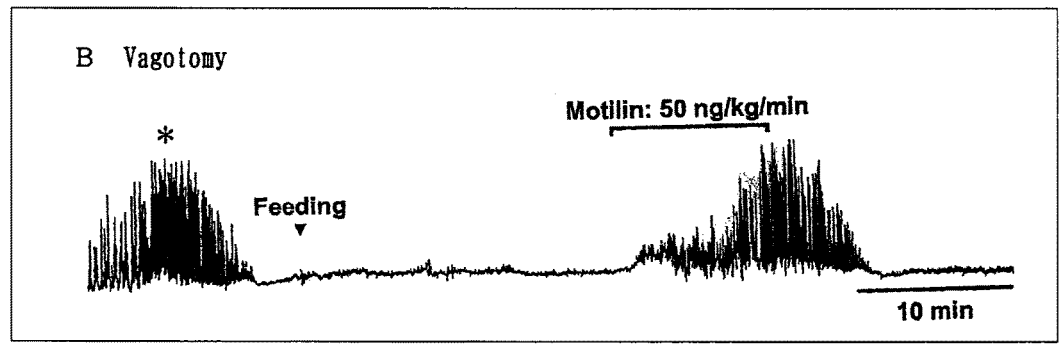
FIG. 8B is a chart showing an action for gastric contractions by administration of motilin after food intake in the vagotomized Suncus murinus.
Figure 8C:
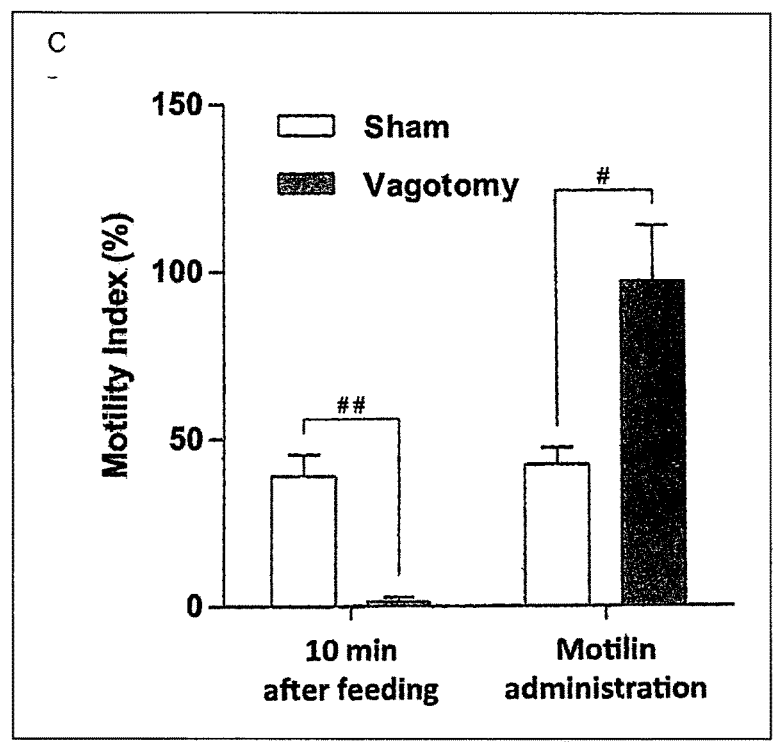
FIG. 8C is a graph showing a motility index during administration of motilin after food intake in the sham-operated Suncus murinus and the vagotomized Suncus murinus.

In the sham-operated *Suncus mirinus*, phase I of MMC changed into non-periodic postprandial contractions after intake of feed, and 10-minute administration of motilin (50 ng/kg/min) did not induce phase III-like contractions (FIG. 8A). In contrast, in the vagotomized *Suncus mirinus*, the intake of feed did not interrupt phase I of MMC, and exogenous motilin induced strong phase III contractions similarly to the action of motilin during fasting (FIG. 8B). The MI in the vagotomized *Suncus murinus* for 10 minutes after initiation of intake of feed was significantly lower than that in the sham-operated *Suncus murinus*, and the MI of postprandial motilin-induced contractions in the vagotomized *Suncus murinus* was significantly higher than that in the sham-operated *Suncus murinus* (FIG. 8C).

As clear from the results, it was revealed that, in the *Suncus murinus*, ghrelin stimulates phase II of MMC via the vagus nerve, the vague nerve is necessary for onset of postprandial gastric contractions, and inhibition of phase III contractions induced by motilin depends on the vagus nerve.

Example 3 (Action on Postprandial Motility by Co-Administration of Ghrelin and Motilin)

(1) Material and Method
A. Drug

Each of *Suncus* motilin (Scrum Inc., Tokyo, Japan) and human ghrelin (Asubio Pharma Co., Ltd., Hyogo, Japan) was dissolved in PBS containing 0.1% bovine serum albumin.

B. Animal

*Suncus murinus* (male, outbred KAT strain, 7 to 39 weeks old, 56 to 91 g) was used for the experiment. The Each animal was bred in a plastic cage provided with an empty can as a nest box under the following conditions: temperature at 23±2° C., illumination between 8:00 and 20:00, and free intake of commercial trout feed (SP, Nippon Formula Feed Mfg Co., Ltd., Yokohama, Japan).

C. Operation (Fixation Suture of Force Transducer and Insertion of Catheter into Jugular Vein)

After 3 hours of fasting, *Suncus murinus* was anesthetized by an intraperitoneal injection of pentobarbital sodium (50 mg/kg). Through a midline incision, the stomach was exposed outside the body, and a force transducer was fixed via suture in the circular muscle direction of the body of stomach. The wire extending from the force transducer was inserted through the abdominal wall, passed under the skin, and exposed at the back of the neck.

An intravenous catheter was inserted in the right jugular, and extracorporeally fixed to the back. The catheter was filled with heparinized saline (100 units/mL) to prevent clotting.

Each of the operated *Suncus murinus* was allowed to recover for several days.

D. Measurement of Gastric Motility

Drug administration and measurement of gastric motility were performed in the conscious, free-moving state without anesthesia.

E. Administration 2 g of feed was given to each *Suncus murinus* fastened (for 8 to 10 hours) for 10 minutes. After the intake of feed for 10 minutes, ghrelin (50, 1,000, or 3,000 ng/kg), motilin (300, 500, 1,000, or 3,000 ng/kg), or a mixed solution of ghrelin (15 or 50 ng/kg) and motilin (100, 200, or 300 ng/kg) was intravenously administered through a jugular vein catheter rapidly.

F. Measurement of Gastric Motility

Amplified analog signals were converted into digital signals by an analog-to-digital converter (ADC-20, Pico Technology Ltd, St Neots, UK), and the digital signals were recorded on a computer.

Phase III contractions of MMC in conscious *Suncus murinus* were defined on the basis of those in dogs and humans (that is, clustered contractions with an amplitude of 8 g or more that lasts for 5 minutes or more).

G. Data Analysis

Gastric motility was quantitated using a motility index ($\Delta$MI). A motility index ($\Delta$MI) based on a drug was calculated using the following equation.

$$\Delta MI\ (\%) = (A-C)/B \times 100$$

A: AUC of contractions for 10 minutes during which the drug was administered
B: AUC of 10-minute spontaneous phase III contractions appeared before administration of the drug
C: (AUC of contractions appeared for 5 minutes between 5 and 10 minutes after the intake of feed)×2

Figure 9:
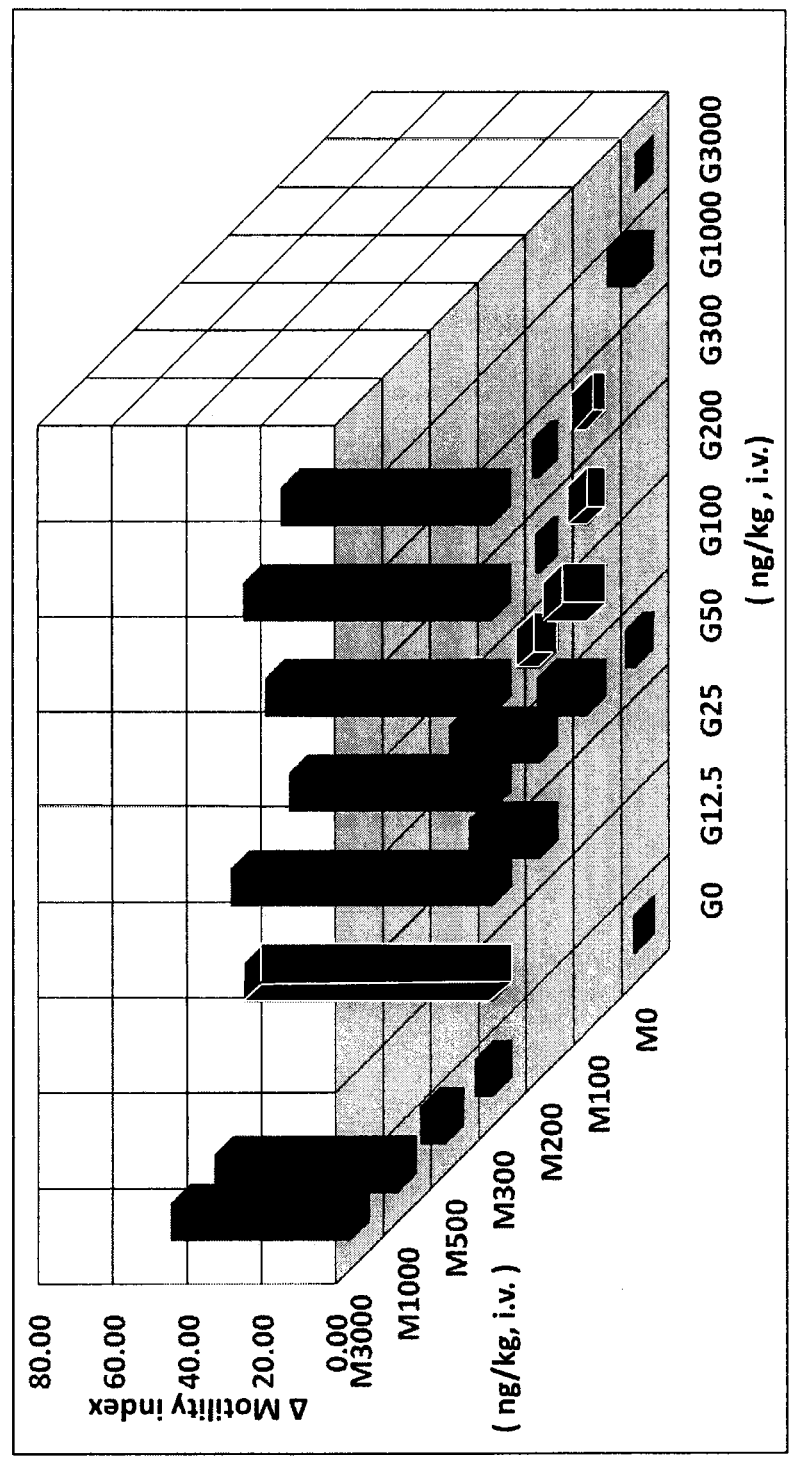
FIG. 9 is a diagram showing the postprandial effect of enhancing gastric motility by co-administration of ghrelin and motilin. G represents ghrelin, M represents motilin, and values following G and M represent dosages.

(2) Results (FIG. 9)
A. Action of Ghrelin Alone 50 ng/kg of ghrelin (G) did not induce contractions of the body of the stomach.
(Motility Index: About 2.8%)
1,000 ng/kg of ghrelin (G) did not induce contractions of the body of the stomach.
(Motility Index: About 7.6%)
3,000 ng/kg of ghrelin (G) did not induce contractions of the body of the stomach.
(Motility Index: About 0.03%)

B. Action of Motilin Alone 300 ng/kg of motilin (M) did not induce contractions of the body of the stomach.
(Motility Index: About 4.9%)
500 ng/kg of motilin (M) did not induce contractions of the body of the stomach.
(Motility Index: About 6.8%)
1,000 ng/kg of motilin (M) induced phase III-like contractions.
(Motility Index: About 49.5%)
3,000 ng/kg of motilin (M) induced phase III-like contractions.
(Motility index: about 48.3%)

C. Action by co-administration of ghrelin (G) and motilin (M)

50 ng/kg of G and 100 ng/kg of M did not induce phase III-like contractions.
(Motility Index: About 13.5%)
100 ng/kg of G and 100 ng/kg of M did not induce phase III-like contractions.
(Motility Index: About 12.1%)
200 ng/kg of G and 100 ng/kg of M did not induce phase III-like contractions.
(Motility Index: About 4.8%)
300 ng/kg of G and 100 ng/kg of M did not induce phase III-like contractions.
(Motility Index: About 3.5%)
25 ng/kg of G and 200 ng/kg of M did not induce phase III-like contractions.
(Motility Index: About 19.4%)
50 ng/kg of G and 200 ng/kg of M induced phase III-like contractions.
(Motility Index: About 24.4%)
100 ng/kg of G and 200 ng/kg of M did not induce phase III-like contractions.

(Motility Index: About 7.9%)
200 ng/kg of G and 200 ng/kg of M did not induce phase III-like contractions.
(Motility Index: About 1.2%)
300 ng/kg of G and 200 ng/kg of M did not induce phase III-like contractions.
(Motility Index: About 2.1%)
12.5 ng/kg of G and 300 ng/kg of M induced phase III-like contractions.
(Motility Index: About 63.5%)
25 ng/kg of G and 300 ng/kg of M induced phase III-like contractions.
(Motility Index: About 70.7%)
50 ng/kg of G and 300 ng/kg of M induced phase III-like contractions.
(Motility Index: About 55.0%)
100 ng/kg of G and 300 ng/kg of M induced phase III-like contractions.
(Motility Index: About 61.3%)
200 ng/kg of G and 300 ng/kg of M induced phase III-like contractions.
(Motility Index: About 67.3%)
300 ng/kg of G and 300 ng/kg of M induced phase III-like contractions.
(Motility Index: About 57.0%)

Example 4 (Action on Postprandial Gastric Emptying by Co-Administration of Ghrelin and Motilin)

(1) Material and Method
A. Drug

Each of *Suncus* motilin (Scrum Inc., Tokyo, Japan) and human ghrelin (Asubio Pharma Co., Ltd., Hyogo, Japan) was dissolved in PBS containing 0.1% bovine serum albumin (hereinafter referred to as 0.1% BSA/PBS).

B. Animal

*Suncus murinus* (male, outbred KAT strain, 7 to 14 weeks old, 60 to 91 g) was used for the experiment. Each animal was bred in a plastic cage provided with an empty can as a nest box under the following conditions: temperature at 23±2° C., illumination between 8:00 and 20:00, and free intake of commercial trout feed (SP, Nippon Formula Feed Mfg Co., Ltd., Yokohama, Japan).

C. Operation (Insertion of Catheter into Jugular Vein)

After 3 hours of fasting, *Suncus murinus* was anesthetized by an intraperitoneal injection of pentobarbital sodium (50 mg/kg). An intravenous catheter was inserted in the right jugular, and extracorporeally fixed to the back. The catheter was filled with heparinized saline (100 units/mL) to prevent clotting.

Each of the operated *Suncus murinus* was allowed to recover for several days.

D. Measurement of Gastric Emptying 1.5 g of feed was given to the *Suncus murinus* fasted for 11 to 12 hours during a phase I period. 10 minutes after starting intake of feed, a 0.1% BSA/PBS solution as a solvent or a mixed solution of ghrelin (50 ng/kg) and motilin (300 ng/kg) that induced strong phase III-like contractions was intravenously administered rapidly. 20 minutes after the administration, the *Suncus murinus* was euthanized by intraperitoneal administration of excess amount of pentobarbital sodium, the pyloric part and the cardiac part were ligated with a suture, and the stomach was excised. The stomach was then opened along the greater curvature, and food in the stomach was collected in a petri dish. The food remaining in the stomach was dried in an incubator at 37° C., and the dry weight of the food was measured after 48 hours by an electronic balance. The residual ratio (%) in the stomach was calculated using (dry weight of the feeds taken out of the stomach/weight of eaten feeds)×100, and evaluated.

E. Statistical Analysis

Un-paird Student's t test was performed. A p value of 0.05 or less was considered to be statistically significant.

Figure 10:
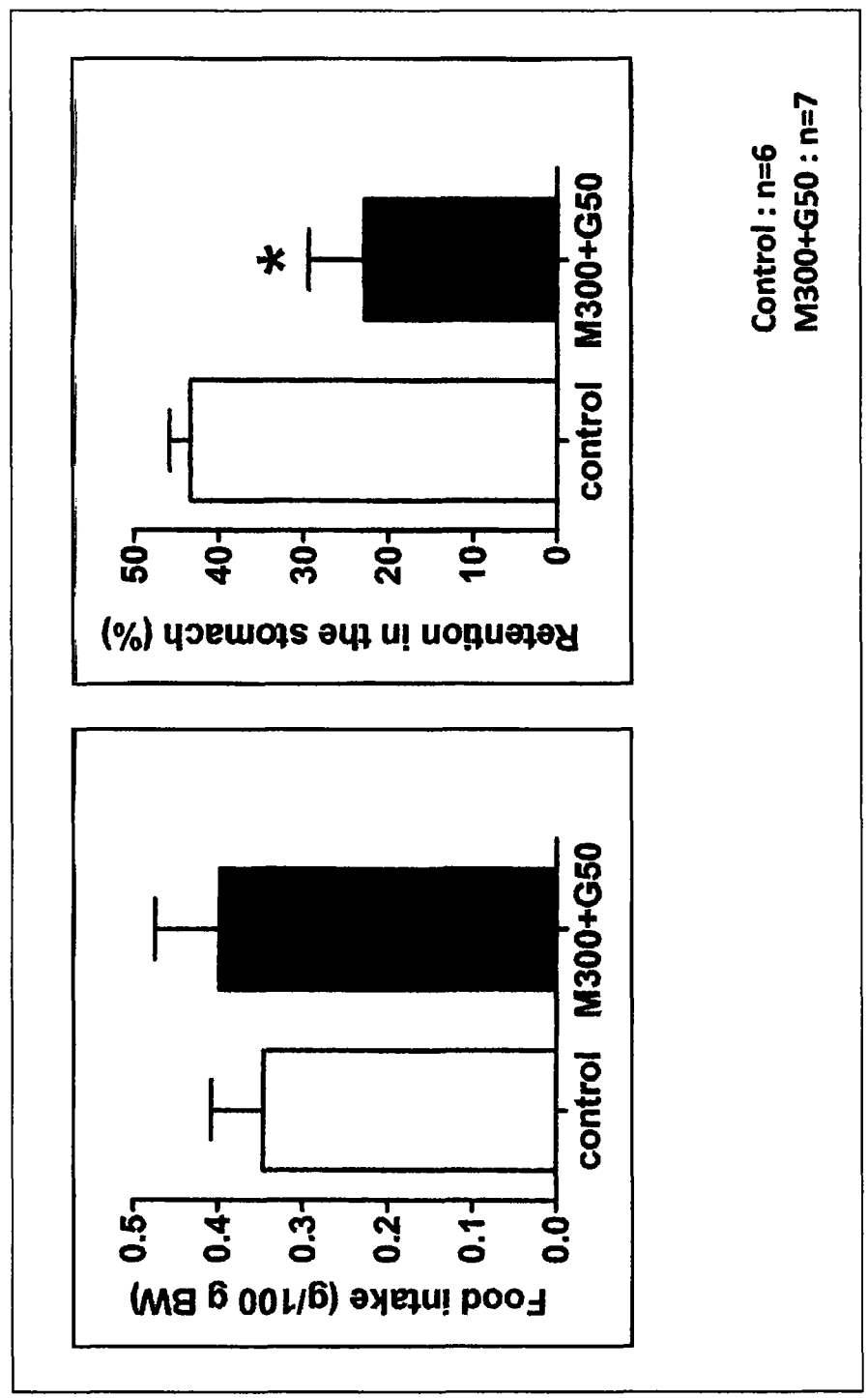
FIG. 10 is graphs showing the postprandial gastric emptying by co-administration of ghrelin and motilin. 0.1% BSA/PBS is used as a control, M300 represents administration of 300 ng/kg of motilin, and G50 represents administration of 50 ng/kg of ghrelin.

(2) Results (FIG. 10)
A. Action by Administration of 0.1% BSA/PBS
0.1% BSA/PBS: The residual ratio in the stomach was 43.4%.
B. Action by Co-Administration of Ghrelin (G) and Motilin (M)
50 ng/kg of G and 300 ng/kg of M: The residual ratio in the stomach was 22.3%.

Example 5 (Action on Postprandial Motility after Meal by Co-Administration of a Ghrelin Agonist and Motilin)

(1) Material and Method
A. Drug

*Suncus* motilin (Scrum Inc., Tokyo, Japan) was dissolved in PBS containing 0.1% bovine serum albumin. A ghrelin agonist (compound in Example 34(a) in WO2009/098901) was dissolved in saline.

B. Animal

*Suncus murinus* (male, outbred KAT strain, 8 to 10 weeks old, 76 to 84 g) was used for the experiment. Each animal was bred in a plastic cage provided with an empty can as a nest box under the following conditions: temperature at 23±2° C., illumination between 8:00 and 20:00, and free intake of commercial trout feed (SP, Nippon Formula Feed Mfg Co., Ltd., Yokohama, Japan).

C. Operation (Fixation Suture of Force Transducer and Insertion of Catheter into Jugular Vein)

After 3 hours of fasting, *Suncus murinus* was anesthetized by an intraperitoneal injection of pentobarbital sodium (50 mg/kg). Through a midline incision, the stomach was exposed outside the body, and a force transducer was fixed via suture in the circular muscle direction of the body of stomach. The wire extending from the force transducer was inserted through the abdominal wall, passed under the skin, and exposed at the back of the neck.

An intravenous catheter was inserted in the right jugular, and extracorporeally fixed to the back. The catheter was filled with heparinized saline (100 units/mL) to prevent clotting.

Each of the operated *Suncus murinus* was allowed to recover for several days.

D. Measurement of Gastric Motility

Drug administration and measurement of gastric motility were performed in the conscious, free-moving state without anesthesia.

E. Administration 2 g of feed was given to each *Suncus murinus* fastened (for 8 to 10 hours) for 10 minutes. After the 10-minute intake of feed, a ghrelin agonist (10 or 30 mg/kg), or a mixed solution of ghrelin agonist (50 or 100 µg/kg) and motilin (300 ng/kg) was intravenously administered through a jugular vein catheter rapidly.

F. Measurement of Gastric Motility

Amplified analog signals were converted into digital signals by an analog-to-digital converter (ADC-20, Pico Technology Ltd, St Neots, UK), and the digital signals were recorded on a computer.

Phase III contractions of MMC in conscious *Suncus murinus* were defined on the basis of those in dogs and humans (that is, clustered contractions with an amplitude of 8 g or more that lasts for 5 minutes or more).

G. Data Analysis

Gastric motility was quantitated using a motility index (ΔMI). A motility index (ΔMI) based on a drug was calculated using the following equation.

$$\Delta MI\ (\%) = (A-C)/B \times 100$$

A: AUC of contractions for 10 minutes during which the drug was administered

B: AUC of 10-minute spontaneous phase III contractions appeared before administration of the drug C: (AUC of contractions appeared for 5 minutes between 5 and 10 minutes after the intake of feed)×2

Figure 11A:
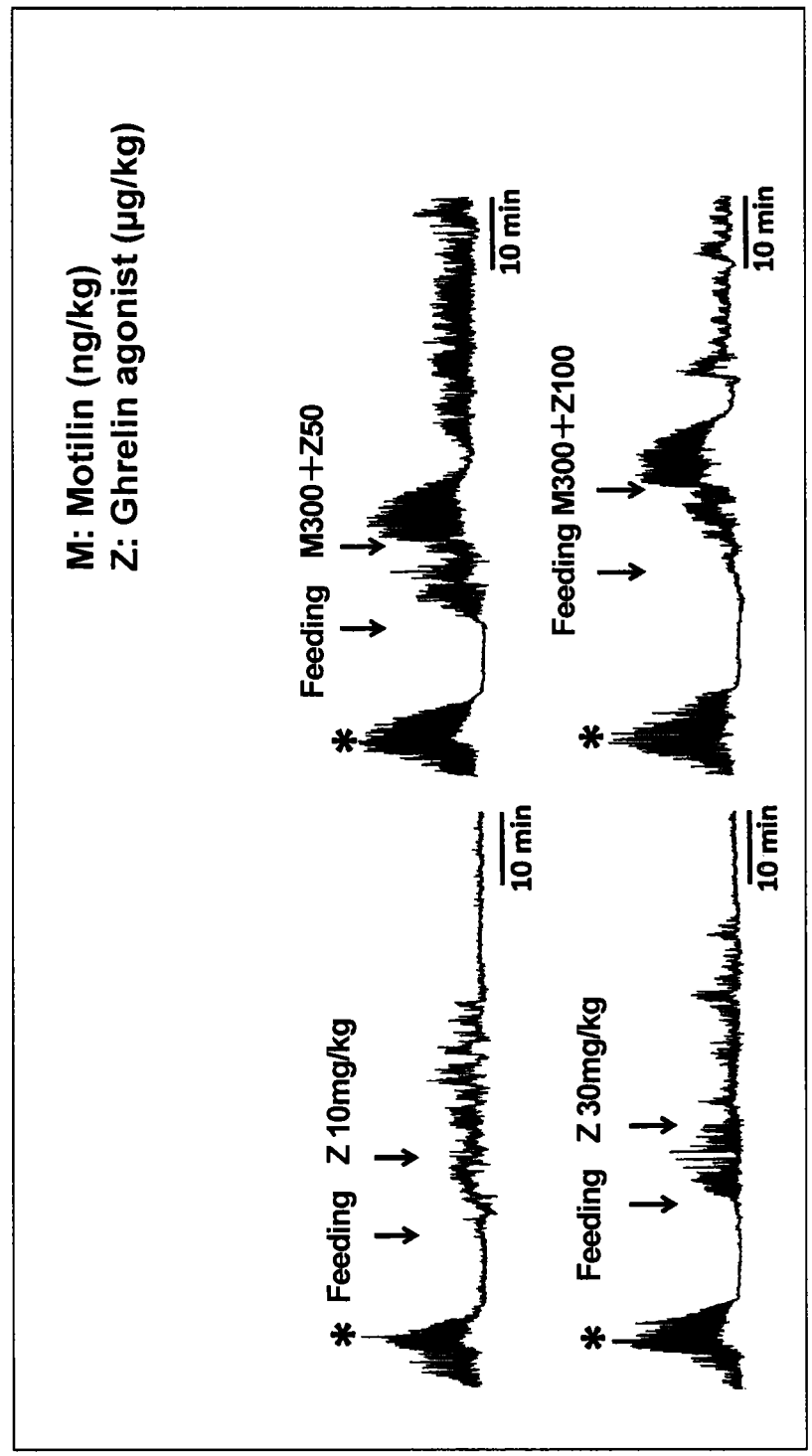
FIG. 11A is charts showing an action for postprandial gastric contractions by co-administration of a ghrelin agonist (Z) and motilin (M). Z represents a ghrelin agonist, and M represents motilin. M300 represents administration of 300 ng/kg of motilin. In administration of ghrelin agonist (Z) alone, Z10 mg and Z30 mg represent administration of 10 mg/kg and 30 mg/kg, respectively. In co-administration of ghrelin agonist (Z) and motilin (M), Z50 and Z100 represent administration of 50 μg/kg and 100 μg/kg, respectively.
Figure 11B:
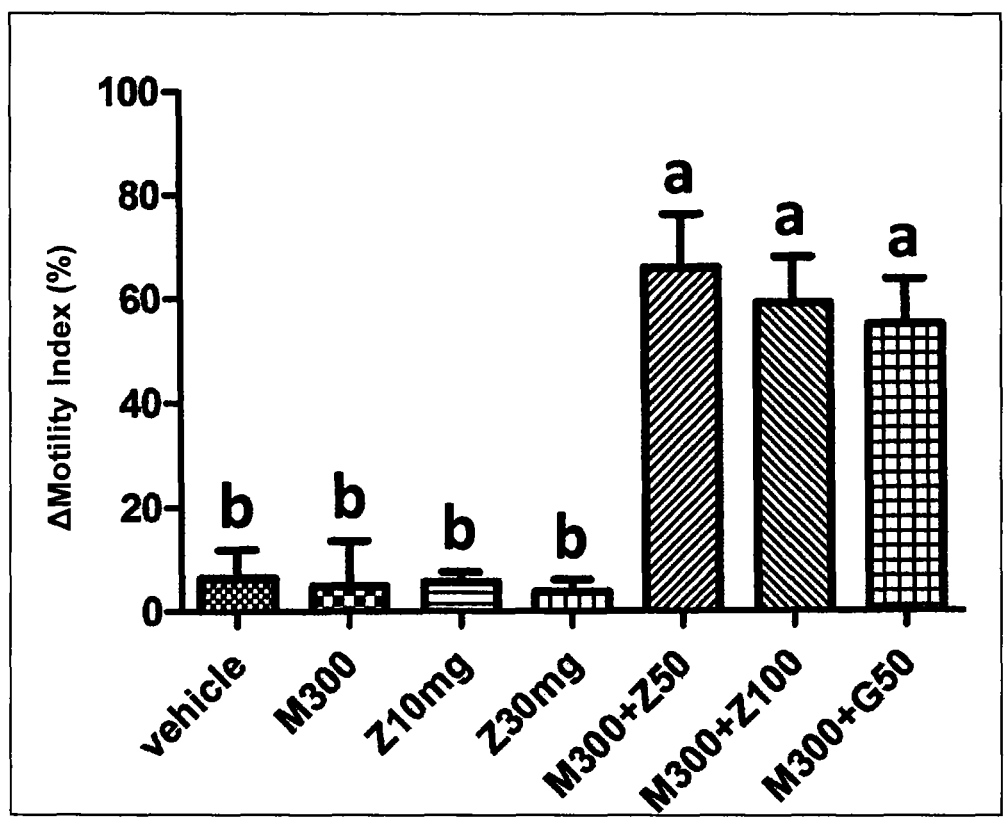
FIG. 11B is a graph showing an action for postprandial gastric contractions by co-administration of a ghrelin agonist (Z) and motilin (M). Z represents a ghrelin agonist, and M represents motilin. M300 represents administration of 300 ng/kg of motilin. In administration of ghrelin agonist (Z) alone, Z10 mg and Z30 mg represent administration of 10 mg/kg and 30 mg/kg, respectively. In co-administration of ghrelin agonist (Z) and motilin (M), Z50 and Z100 represent administration of 50 μg/kg and 100 μg/kg, respectively.

(2) Results (FIGS. 11A and 11B)

A. Action of Ghrelin Agonist Alone 10 mg/kg of ghrelin agonist (Z) did not induce contractions of the body of the stomach.

(Motility Index: About 5.7%)

30 mg/kg of ghrelin agonist (Z) did not induce contractions of the body of the stomach.

(Motility Index: About 3.7%)

B. Action by Co-Administration of Ghrelin Agonist (Z) and Motilin (M)

50 μg/kg of Z and 300 ng/kg of M induced phase III-like contractions.

(Motility Index: About 65.9%)

100 μg/kg of Z and 300 ng/kg of M induced phase III-like contractions.

(Motility Index: About 59.1%)

The invention claimed is:

1. A method for enhancing postprandial gastric motility, comprising:
    administering an ingredient (A) which is ghrelin or a ghrelin agonist and an ingredient (B) which is motilin or a motilin agonist to a subject in need thereof such that an effective blood level of each of the ingredients (A) and (B) is achieved after food intake,
    wherein after food intake is within about 30 minutes immediately after intake of a meal,
    timing of the administering of each of the ingredients (A) and (B) is determined in consideration of a time to achieve the effective blood level, which is about 20 minutes to about 60 minutes after oral administration and about 10 minutes after intravenous administration, and
    in the administering of the ingredient (A) and the ingredient (B), the dose of the ingredient (A) is 1/50 to 1/500 of an effective dose for administering the ingredient (A) alone, and the dose of the ingredient (B) is 1/3 to 1/30 of an effective dose for administering the ingredient (B) alone.

2. The method according to claim 1, which treats a disease selected from the group consisting of diabetic gastroparesis, postoperative gastroparesis, and functional dyspepsia.

3. The method according to claim 1, which treats diabetic gastroparesis.

4. The method according to claim 1, wherein the administering comprises orally administering the ingredients (A) and (B) from about 30 minutes before to immediately before intake of a meal such that the effective blood level is achieved about 20 minutes to about 60 minutes after oral administration of the ingredients (A) and (B), respectively.

5. The method according to claim 4, wherein the administering comprises orally administering the ingredients (A) and (B) simultaneously.

6. The method according to claim 1, wherein the administering comprises intravenously administering the ingredients (A) and (B) immediately after food intake such that the effective blood level is achieved about 10 minutes after intravenous administration of the ingredients (A) and (B), respectively.

7. The method according to claim 6, wherein the administering comprises intravenously administering the ingredients (A) and (B) simultaneously.

8. The method according to claim 1, wherein the administering comprises administering ghrelin at a dose of 1.5 to 20 μg per intravenous administration per adult human patient.

9. The method according to claim 1, wherein the administering comprises administering ghrelin at a dose of 2 to 6 μg per intravenous administration per adult human patient.

10. The method according to claim 8, wherein the administering comprises administering motilin at a dose of 6 to 40 μg per intravenous administration per adult human patient.

11. The method according to claim 9, wherein the administering comprises administering motilin at a dose of 9 to 20 μg per intravenous administration per adult human patient.

12. A method of treating a human patient having a disease selected from the group consisting of diabetic gastroparesis, postoperative gastroparesis, and functional dyspepsia, comprising:
    administering ghrelin or a ghrelin agonist and motilin or a motilin agonist to the human patient,
    wherein the dose of ghrelin or a ghrelin agonist is 1/50 to 1/500 of an effective dose for administering ghrelin or the ghrelin agonist alone, and the dose of motilin or a motilin agonist is 1/3 to 1/30 of an effective dose for administering motilin or the motilin agonist alone.

13. The method of claim 12, wherein diabetic gastroparesis is treated.

14. The method of claim 12, wherein postoperative gastroparesis is treated.

15. The method of claim 12, wherein functional dyspepsia is treated.

16. The method of claim 12, wherein the administering comprises administering ghrelin at a dose of 2 to 6 μg per intravenous administration per adult.

17. The method of claim 12, wherein the administering comprises administering motilin at a dose of 9 to 20 μg per intravenous administration per adult.

18. The method of claim 12, wherein the administering comprises simultaneously administering ghrelin and motilin.

19. The method of claim 12, wherein the administering comprises simultaneously administering ghrelin at a dose of 2 to 6 μg per intravenous administration per adult and motilin at a dose of 9 to 20 μg per intravenous administration per adult.

* * * * *